United States Patent [19]
Flaugh et al.

[11] Patent Number: 5,229,409
[45] Date of Patent: Jul. 20, 1993

[54] 6-SUBSTITUTED-TETRAHYDROBENZ[C-D]INDOLES

[75] Inventors: Michael E. Flaugh; Michael J. Martinelli, both of Indianapolis; John M. Schaus, Zionsville, all of Ind.

[73] Assignee: Eli Lilly and Company, Indianapolis, Ind.

[21] Appl. No.: 725,175

[22] Filed: Jul. 3, 1991

Related U.S. Application Data

[63] Continuation-in-part of Ser. No. 567,990, Aug. 15, 1990, abandoned.

[51] Int. Cl.$^5$ .................... C07D 209/90; A61K 31/40
[52] U.S. Cl. .................................. 514/411; 548/406; 548/421; 548/436
[58] Field of Search ........................ 548/436; 514/411

[56] References Cited

U.S. PATENT DOCUMENTS

| | | | |
|---|---|---|---|
| 3,336,307 | 8/1967 | Shen | 268/247.2 |
| 3,671,541 | 6/1972 | Bormann et al. | 260/309.6 |
| 3,674,801 | 7/1972 | Bormann et al. | 260/309.6 |
| 4,057,560 | 11/1977 | Bormann et al. | 260/326.86 |
| 4,110,339 | 8/1978 | Bach et al. | 548/436 |
| 4,252,803 | 2/1981 | Webb | 424/218.5 |
| 4,282,240 | 8/1981 | Baldwin et al. | 424/274 |
| 4,447,438 | 5/1984 | Ledelec et al. | 424/267 |
| 4,576,959 | 3/1986 | Flaugh | 514/411 |
| 4,745,126 | 5/1988 | Leander | 514/411 |
| 4,983,622 | 1/1981 | Flaugh | 514/411 |
| 5,021,438 | 6/1991 | Junge et al. | 548/436 |
| 5,039,820 | 8/1991 | Kress et al. | 548/436 |
| 5,096,908 | 3/1992 | Gidda et al. | 514/307 |

FOREIGN PATENT DOCUMENTS

| | | | |
|---|---|---|---|
| 091328A2 | 10/1983 | European Pat. Off. | |
| 148440 | 12/1984 | European Pat. Off. | |
| 0153083 | 8/1985 | European Pat. Off. | |
| 162695 | 11/1985 | European Pat. Off. | 548/436 |
| 332968 | 9/1989 | European Pat. Off. | 548/436 |
| 517732 | 2/1972 | Fed. Rep. of Germany | |
| 3525564A1 | 7/1985 | Fed. Rep. of Germany | |

OTHER PUBLICATIONS

Fuller et al., *Advances in Drug Research*, 17, pp. 349–380 (1988).
Glennon et al., *J. Med. Chem.*, 30, pp. 1–12 (1987).
Gonzalez-Heydrich et al., *J. Clin. Psychiatry*, 51, pp. 5–12 (1990).
Saxena et al., *J. of Cardiovasc. Pharmacol.*, 15, pp. 517–534 (1990).
Dreteler et al., *J. Card. Pharm.*, 14, 770 (1989).
Dreteler et al., *J. Card. Pharm.*, 17, 488 (1991).
Shepheard et al., *Eur. J. Pharm.*, 186, 267 (1990).
Lucot et al., *Pharm. Biochem. & Beh.*, 33, 627 (1989).
Othmer et al., *J. Clin. Psych.*, 48(5), 201 (1987).
Bowen et al., *Ann. Neurol.*, 32, 112 (1992).
Bowen et al., *The Lancet*, 339, 132 (1992).
Bowen et al., *Trends in Neurosciences*, 15, 84 (1992).
Prehn et al., *Eur. J. Pharm.*, 203, 213 (1991).
Dourish et al., *Psychopharmacology*, 86, 197 (1985).
Hutson et al., *Eur. J. Pharm.*, 129, 347 (1986).
Dourish et al., *Psychopharmacology*, 94, 58 (1988).
Dourish et al., *Brain 5-HT$_{1A}$ Receptors: Behavioral and Neurochemical Pharmacology*, Chapter 18, Ellis Harwood, publisher.
Dourish et al., *Brain Res. Bull.*, 15, 377 (1985).
Montgomery et al., *Psychopharmacology*, 94, 110 (1988).
Hutson et al., *Eur. J. Pharm.*, 150, 361 (1988).
Dourish et al., *Appetite*, 7, Suppl., 127 (1986).
Gilbert et al., *Psychopharmacology*, 93, 349 (1987).
Dourish et al., *Psychopharmacology*, 95, 185 (1988).
Neill et al., *Eur. J. Pharm.*, 151, 329 (1988).
Dourish et al., *Brain 5-HT$_{1A}$ Receptors: Behavioral and Neurochemical Pharmacology*, Chapter 20, Ellis Harwood, publisher (1987).

(List continued on next page.)

*Primary Examiner*—Emily Bernhardt
*Attorney, Agent, or Firm*—Douglas J. Taylor; Leroy Whitaker; David E. Boone

[57] ABSTRACT

The present invention involves certain 4-amino-6-substituted-tetrahydrobenz[cd]indoles and their use in treating disorders which can be benefited by modifying 5-HT A receptor function.

21 Claims, No Drawings

OTHER PUBLICATIONS

Hilleman et al., *Arch. Intern. Med.*, 152, 350 (1992).
McBride et al., *Pharm. Bio. and Beh.*, 34, 381 (1989).
Flaugh et al., *J. Med. Chem.*, 31, 1746–1753 (1988).
Kruse et al., *J. Org. Chem.*, 49, 4761–4768 (1984).
Bach et al., *J. Med. Chem.*, 23, 481–491 (1980).
Derwent Abstract 57337, For FR 2,471,373.
Haefliger et al., *Tet. Lett.*, 25(3), 289 (1984).
Somei et al., Chemical Abstracts, 107, 39610b for JP62-63,567.
T. W. Greene, *Protective Groups in Organic Synthesis*, Chapter 7, John Wiley and Sons, New York (1973).
J. W. Barton, *Protective Groups in Organic Synthesis*, Chapter 2, McOmie, ed., Plenum Press, New York, (1973).
*The Vocabulary of Organic Chemistry*, Orchin et al., John Wiley and Sons., Inc., publishers, p. 126.
A. Schoenberg et al., *J. Org. Chem.*, 39, 3327 (1974).
A. Schoenberg et al., *J. Org. Chem.*, 39, 3318 (1974).
Raucher et al., *Tet. Lett.*, 21, 4061 (1980).
Nichols et al., *Org. Prep. & Proc. Ind.*, 9, 277 (1977).
Leanna et al., *Tet. Lett.*, 30, 3935 (1989).
O. Mitsunobu, *Synthesis*, Jan. 1981, p. 1.
J. P. Freemer et al., *Synthesis*, Dec. 1974, p. 894.
Sugi et al., *Bull. Chem. Soc. Jap.*, 43, p. 1489 (1970).
Morrison & Boyd, Chapter 22, *Organic Chemistry*, 3rd Ed. (1973).
Wong et al., *J. Neural Transm.*, 71, 207–218 (1988).
Wong et al., *J. Neural Transm.*, 64, 251–269 (1985).

6-SUBSTITUTED-TETRAHYDROBENZ[CD]INDOLES

This application is a continuation-in-part of application Ser. No. 07/567,990 filed Aug. 15, 1990, now abandoned.

FIELD OF THE INVENTION

This invention relates to the fields of synthetic organic chemistry and pharmaceutical chemistry and involves tetrahydrobenz[cd]indoles which are useful in treating conditions requiring regulation of the serotonin function in the body.

BACKGROUND OF THE INVENTION

Over the last several years it has become apparent that the neurotransmitter serotonin (5-hydroxytryptamine-5-HT) is associated directly or indirectly with a number of physiological phenomena, including appetite, memory, thermoregulation, sleep, sexual behavior, anxiety, depression, blood pressure lowering and hallucinogenic behavior [Glennon, R. A., *J. Med Chem.*, 30, 1 (1987)].

It has been recognized that there are multiple types of 5HT receptors. These receptors have been classified as 5-HT$_1$, 5-HT$_2$, and 5-HT$_3$ receptors, with the former being further divided into the sub-classes 5-HT$_{1A}$, 5-HT$_{1B}$, 5-HT$_{1C}$, and 5-HT$_{1D}$. The binding affinity of a compound for one or more 5-HT receptors can provide a desirable physiological effect or minimize an undesirable effect. Therefore it is desirable to provide compounds which can bind to 5-HT receptors to act as serotonin agonists or antagonists.

Flaugh in U.S. Pat. No. 4,576,959 (issued 1986) and in European Patent Application 0153083 (published 1985) disclosed a family of 6-substituted-4-dialkylamino-1,3,4,5-tetrahydrobenz[cd]indoles which are described as central serotonin agonists. Leander in U.S. Pat. No. 4,745,126 (1988) disclosed a method for treating anxiety in humans employing a 4-substituted-1,3,4,5-tetrahydrobenz[cd]indole-6-carboxamide derivative.

It has now been found that certain 6- substituted-and particularly the 6-acyl substituted-4- aminotetrahydrobenz[cd]indoles are useful in treating conditions which can be benefited by a modification of 5-HT$_{1}$A receptor function in the body. It has been further found that certain of the instant compounds have substantial affinity for the 5-HT$_{1D}$ receptor and can be useful in treating conditions which can be benefitted by modifying 5-HT$_{1A}$ or 5HT$_{1A}$ and 5-HT$_{1D}$ receptor function in the body.

SUMMARY OF THE INVENTION

This invention relates to a compound of the Formula

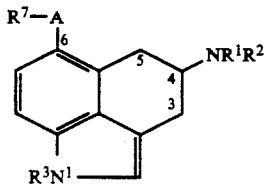

wherein:

R$^1$ is hydrogen, C$_1$–C$_4$ alkyl, C$_3$–C$_4$ alkenyl, cyclopropylmethyl, phenyl-substituted C$_1$–C$_4$ alkyl, —COR$^4$, —(CH$_2$)$_n$S(C$_1$–C$_4$ alkyl), or —(CH$_2$)$_n$CONR$^5$R$^6$;

R$^2$ is hydrogen, C$_1$–C$_4$ alkyl, C$_3$–C$_4$ alkenyl, or cyclopropylmethyl;

R$^3$ is hydrogen, C$_1$–C$_4$ alkyl or a blocking group;

n is 1–4;

R$^4$ is hydrogen, C$_1$–C$_4$ alkyl, C–C$_4$ haloalkyl, C$_1$–C$_4$ alkoxy or phenyl;

R$^5$ and R$^6$ are independently hydrogen, a C$_1$–C$_4$ alkyl, or a C$_5$–C$_8$ cyclalkyl;

R$^7$ is C$_1$–C$_8$ alkyl, substituted C$_1$–C$_8$ alkyl, aryl, substituted aryl, aryl (C$_1$–C$_4$ alkyl), substituted aryl (C$_1$–C$_4$ alkyl), C$_3$–C$_7$ cycloalkyl-substituted methyl, or C$_3$–C$_7$ cycloalkyl with the proviso that when A is C≡C then R$^7$ is C$_1$–C$_7$ alkyl, substituted C$_1$–C$_7$ alkyl, aryl, substituted aryl, aryl (C$_1$–C$_3$ alkyl), substituted aryl (C$_1$–C$_3$ alkyl), or C$_3$–C$_7$ cyclalkyl;

A is C=O, CHOH or C≡C; or a pharmaceutically acceptable salt thereof.

A further embodiment of the instant invention comprises a compound of Formula I wherein (a) R$^1$ and R$^2$ are independently hydrogen or C$_1$–C$_4$ alkyl; (b) R$^3$ is hydrogen; (c) A is C=O; and (d) R$^7$ is C$_1$–C$_8$ alkyl, substituted C$_1$–C$_8$ alkyl, phenyl, or phenyl substituted (C$_1$–C$_4$ alkyl); and pharmaceutically acceptable salts thereof.

The invention also provides a pharmaceutical formulation comprising a compound of Formula I and a pharmaceutically acceptable excipient therefor.

A further embodiment of the invention is a method for effecting a biological response at a 5-HT receptor by administering an effective amount of a compound of Formula I. Further embodiments involve the treatment of disease states with require regulation of serotonin function in the body.

DETAILED DESCRIPTION OF THE INVENTION

As used herein, the term "alkyl" represents a straight or branched alkyl chain having the indicated number of carbon atoms. For example, "C$_1$–C$_4$ alkyl" groups are methyl, ethyl, n-propyl, isopropyl, n-butyl, sec.-butyl, isobutyl and tert-butyl. "C$_1$–C$_8$ alkyl" groups include these listed for C$_1$–C$_4$ alkyl as well as n-pentyl, 2-methylbutyl, 3-methylbutyl, n-hexyl, 4-methylpentyl, n-heptyl, 3-ethylpentyl, 2-methylhexyl, 2,3-dimethylpentyl, n-octyl, 3-propylpentyl, 6-methyl-heptyl, and the like.

The term "C$_3$–C$_4$ alkenyl" refers to olefinically unsaturated alkyl groups such as —CH$_2$CH=CH$_2$, —CH(CH$_3$)CH=CH$_2$, —CH$_2$CH$_2$CH=CH$_2$ and the like.

The term "aryl" means an aromatic carbocyclic structure having a cyclic structure of one or two rings with a total of six to ten carbon atoms in the cyclic structure. Examples of such ring structures are phenyl, naphthyl, indonyl, and the like.

The term "cycloalkyl" means an aliphatic carbocyclic structure having the indicated number of carbon atoms in the ring. For example, the term "C$_1$–C$_7$ cycloalkyl" means cyclopropyl, cyclobutyl, cyclopentyl, cyclohexyl, and cycloheptyl.

The term "aryl (C$_1$–C$_4$ alkyl)" means an aromatic carbocyclic structure joined to a C$_1$–C$_4$ alkyl group. Examples of such groups are benzyl, phenylethyl, α-methylbenzyl, 3-phenylpropyl, α-naphthylmethyl, β-naphthylmethyl, 4-phenylbutyl, and the like. Similarly the term "aryl (C$_1$-C$_3$ alkyl)" means an aromatic carbocyclic structure joined to a C$_1$-C$_3$ alkyl.

The C$_1$-C$_8$ alkyl, the aryl, the aryl (C$_1$-C$_4$ alkyl) groups, and aryl (C$_1$-C$_3$ alkyl) can be substituted by one or two moieties. Typical aryl and/or alkyl substituents are C$_1$-C$_3$ alkoxy, halo, hydroxy, C$_1$-C$_3$ thioalkyl, and the like. Moreover, the aryl, aryl (C$_1$-C$_4$ alkyl) and aryl (C$_1$-C$_3$ alkyl) groups may also be substituted by a C$_1$-C$_3$ alkyl or a trifluoromethyl group.

In the foregoing, the term "C$_1$-C$_3$ alkyl" means any of methyl, ethyl, n-propyl, and isopropyl; the term "C$_1$-C$_3$ alkoxy" means any of methoxy, ethoxy, n-propoxy, and isopropoxy; the term "halo" means any of fluoro, chloro, bromo, and iodo; and the term "C$_1$-C$_3$ thioalkyl" means any of methylthio, ethylthio, n-propylthio, and isopropylthio.

Examples of substituted C$_1$-C$_8$ alkyl are methoxymethyl, trifluoromethyl, 6-chlorohexyl, 2-bromopropyl, 2-ethoxy-4-iodobutyl, 3-hydroxypentyl, methylthiomethyl, and the like.

Examples of substituted aryl are p-bromo-phenyl, m-iodophenyl, p-tolyl, o-hydroxyphenyl, β-(4-hydroxy)naphthyl, p-(methylthio)phenyl, m-trifluoro- methylphenyl, 2-chloro-4-methoxyphenyl, α-(5-chloro)- naphthyl, and the like.

Examples of the substituted aryl (C$_1$-C$_4$ alkyl) are p-chlorobenzyl, o-methoxybenzyl, m-(methylthio)-α-methylbenzyl, 3-(4'- trifluoromethylphenyl)-propyl, o-iodobenzyl, p- methylbenzyl, and the like.

The term "blocking group" is used as it is frequently used in synthetic organic chemistry, to refer to a group which can bond to a nitrogen such as in an amino group and prevent the nitrogen from participating in a reaction carried out on some other functional group of the molecule, but which can be removed from the nitrogen when it is desired to do so. Such groups are discussed by T. W. Greene in chapter 7 of *Protective Groups in Organic Synthesis*, John Wiley and Sons, New York, 1981, and by J. W. Barton in chapter 2 of *Protective Groups in Organic Chemistry*, J. F. W. McOmie, ed., Plenum Press, New York, 1973, which are incorporated herein by reference in their entirety. Examples of such groups include those of the formula —COOR where R includes such groups as methyl, ethyl, propyl, isopropyl, 2,2,2-trichloroethyl, 1-methyl-1- phenylethyl, isobutyl, t-butyl, t-amyl, vinyl, allyl, phenyl, benzyl, p-nitrobenzyl, o-nitrobenzyl, and 2,4-dichlorobenzyl, benzyl and substituted benzyl such as 3,4-dimethoxybenzyl, o-nitrobenzyl, and triphenylmethyl; acyl groups and substituted acyl such as formyl, acetyl, chloracetyl, dichloracetyl, trichloracetyl, trifluoroacetyl, benzoyl, and p-methoxybenzoyl; and other groups such as methanesulfonyl, p-toluenesulfonyl, p-bromobenzenesulfonyl, p-nitrophenylethyl, and p-toluenesulfonylaminocarbonyl. Preferred blocking groups are benzyl (—CH$_2$C$_6$H$_5$), triphenylmethyl (trityl), acyl [C(O)R] or SiR$_3$ where R is C$_1$-C$_4$ alkyl, halomethyl, 2-halo-substituted alkoxy, or phenyl. Particularly preferred blocking groups are —CO$_2$CH$_2$CCl$_3$ and triphenylmethyl.

The compounds of the instant invention have at least one chiral center and therefore at least two stereoisomers can exist for each. A chiral center exists at position 4 as in Formula I. If a substituent group contains a chiral center, then additional stereoisomers can of course exist. Racemic mixtures as well as the substantially pure stereoisomers of Formula I are contemplated as within the scope of the present invention. By the term "substantially pure", it is meant that at least about 90 mole percent, more preferably at least about 95 mole percent and most preferably at least 98 mole percent of the desired stereoisomer is present compared to other possible stereoisomers.

The terms "R" and "S" are used herein as commonly used in organic chemistry to denote specific configuration of a chiral center. The term "R" refers to "right" and refers that configuration of a chiral center with a clockwise relationship of group priorities (highest to second lowest) when viewed along the bond toward the lowest priority group. The term "S" or "left" refers to that configuration of a chiral center with a counterclockwise relationship of group priorities (highest to second lowest) when viewed along the bond toward the lowest priority group. The priority of groups is based upon their atomic number (heaviest isotope first). A partial list of priorities and a discussion of stereo chemistry is contained in the book: *The Vocabulary of Organic Chemistry*, Orchin, et al., John Wiley and Sons Inc., publishers, page 126, which is incorporated herein by reference.

While all of the compounds of the invention are useful for the purposes taught herein, certain of the present compounds are preferred for such uses. Preferably R$^1$ and R$^2$ are both C$_1$-C$_4$ alkyl, and especially n-propyl. R$^3$ is preferably hydrogen, R$^7$ is preferably C$_1$-C$_4$ alkyl, substituted C$_1$-C$_4$ alkyl, or C$_3$-C$_7$ cycloalkyl, Although compounds in which A is CHOH or C≡C have activity, their primary purpose is as intermediates in the preparation of compounds in which A is C=O. Other preferred aspects of the present invention are noted hereinafter.

As pointed out above, this invention includes the pharmaceutically-acceptable salts of the compounds of Formula I. Since the compounds of this invention are amines, they are basic in nature and accordingly react with any number of inorganic and organic acids to form pharmaceutically acceptable salts such as hydro-chloric acid, nitric acid, phosphoric acid, sulfuric acid, hydrobromic acid, hydroidic acid, phosphorous acid and others, as well as salts derived from non-toxic organic acids such as aliphatic mono and dicarboxylic acids, amino acids, phenyl-substituted alkanoic acids, hydroxyalkanoic and hydroxyalkandioic acid, aromatic acids, aliphatic and aromatic sulfonic acids. Such pharmaceutically-acceptable salts thus include sulfate, pyrosulfate, bisulfate, sulfite, bisulfite, nitrate, phosphate, monohydrogenphosphate, dihydrogenphsophate, metaphosphate, pyrophosphate, chloride, bromide, iodide, acetate, propionate, caprylate, acrylate, formate, tartrate isobutyrate, caprate, heptanoate, propiolate, oxalate, malonate, succinate, suberate, sebacate, fumarate, maleate, mandelate, butyne-1,4-dioate, hexyne-1,6-dioate, hippurate, benzoate, chlorobenzoate, methylbenzoate, phthalate, terephthalate, benzenesulfonate, toluenesulfonate, chlorobenzenesulfonate, xylenesulfonate, phenylacetate, phenylpropionate, phenylbutyrate, citrate, lactate, β-hydroxybutyrate, glycolate, malate, naphthalaene-1-sulfonate, naphthalene-2-sulfonate and mesylate.

The following list illustrate representative compounds of the present invention:

4-(di-n-propylamino)-6-acetyl-1,3,4,5-tetrahydrobenz[cd]indole;

4-(di-n-propylamino)-6-(2,2-dimethylpropanoyl)-1,3,4,5-tetrahydrobenz[cd]indole;

4(diethylamino)-6-propanoyl-1,3,4,5-tetrahydrobenz[cd]indole;

4-(di-n-propylamino)-6-benzoyl-1,3,4,5-tetrahydrobenz[cd]indole;

4-(n-propylamino)-6-(2-methylpropanoyl)-1,3,4,5-tetrahydrobenz[cd]indole;

1-methyl-4-(di-n-propylamino)-6-benzoyl-1,3,4,5-tetrahydrobenz[cd]indole;

1-methyl-4-(n-propylamino)-6-(3-methylbutanoyl)-1,3,4,5-tetrahydrobenz[cd]indole;

4-(di-n-propylamino)-6-(2,2-dimethyl-propanoyl)-1,3,4,5-tetrahydrobenz[cd]indole;

4-(di-n-propylamino)-6-(2-phenylethanoyl)-1,3,4,5-tetrahydrobenz[cd]indole;

4-(N-n-propyl-N-cyclopropylmethyl)amino-6-propyanoyl-1,3,4,5-tetrahydrobenz[cd]indole; and 4-(di-n-propylamino)-6-(2-methoxyethanoyl)-1,3,4,5-tetrahydrobenz[cd]indole.

Scheme 1 depicts a process for preparing compounds of the present invention wherein $R^1$, $R^2$ and $R^7$ are as defined above and Z is an amino-blocking group as defined hereinabove.

According to one route of this process, a 4-amino-6-bromotetrahydrobenz[cd]indole 1 is combined with an equimolar to slight excess amount of potassium hydride in diethyl ether. The reagents are generally combined at a cold temperature, typically in the range of about $-20°$ C. to about 10° C., preferably at about 0° C. The resulting mixture is cooled to a temperature in the range of about $-100°$ C. to about $-60°$ C., preferably at about $-78°$ C., and combined with a lithiating reagent, preferably in at least a two molar excess amount. Suitable lithiating reagents include sec-butyllithium, the preferred t-butyllithium, and other similar organolithium compounds is preferred. The reaction is preferably conducted at a temperature in the range of about $-100°$ C. to about $-20°$ C., more preferably at about $-60°$ C. to about $-40°$ C.

The 4-amino-6-lithiotetrahydrobenz[c,d]indole 2 thus prepared is then contacted with an appropriate electrophile such as L—C(O)$R^7$ wherein $R^7$ is defined above and L is a good leaving group such as chlorine bromine, methoxy, phenoxy and the like. Typically, a solution of the compound 2 at a temperature in the range of about $-100°$ C. to about $-60°$ C., preferably at about $-80°$ C., is added to a solution of this reagent in a mutual solvent. It an excess amount of the electrophile is employed in the reaction, the 1-amino group is also acylated (i.e. Z is the acyl group $R^7$C(O) in compound 3a) and a subsequent hydrolysis reaction is required to provide the free indole, I. A 1:1 ratio of electrophile to lithiated indole (compound 2) can be used to minimize acylation of the 1-nitrogen. The reaction is preferably conducted at a temperature in the range of about $-40°$ C. to about 10° C. The desired compound is purified by quenching the reaction mixture with, for example, ice water, when a 1:1 ratio is used. With a higher ratio in which significant 1-acylation is obtained, the product is hydrolyzed using an acid such as phosphoric acid or a base such as sodium carbonate or sodium hydroxide. The mixture is then washed with a water-immiscible organic solvent. The organic phase is extracted with acid; the aqueous phases are combined and made basic; and the desired compound is extracted with a water immiscible organic solvent. The organic solvent is then concentrated, typically under vacuum, and the desired compound I is further purified, if necessary, by standard procedures.

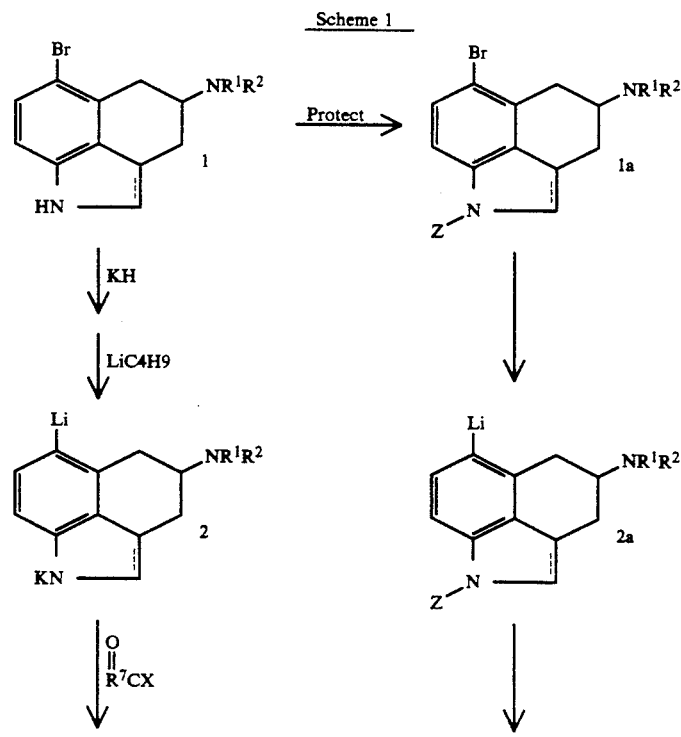

Scheme 1

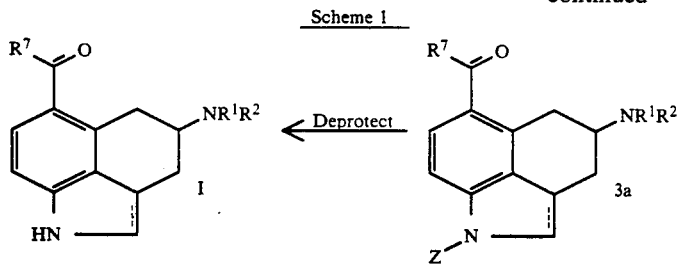

In an alternative route, the 1-nitrogen can be "blocked" or "protected" before initiating the metallation reaction. A blocking group (depicted as "Z") such as $SiR_3$ or $CH_2(C_6H_5)$ where R is $C_3$–$C_4$ alkyl, preferably triisopropyl or phenyl ($C_6H_5$) is preferably used for indole reactants with a trityl group preferably used for indoline reactants. Compound 1a is then reacted with a lithiating agent as described above to provide compound 2a. Compound 2a can then be acylated by contacting with a suitable electrophile as described hereinbove. The resulting compound 3a is then deprotected by treatment with a fluoride salt when Z is $SiR_3$, or when Z is benzyl compound 3a can be subjected to hydrogenolysis over a catalyst such as palladium to remove the benzyl group. The desired compound is isolated by standard conditions and purified by crystallization from common solvents or column chromatography over solid supports such as silica gel or alumina.

An alternative synthesis of the compounds I is depicted in Scheme 2 and involves treatment of the 6-lithio derivatives 2 and 2a (depicted in Scheme 1) with an aldehyde, $R^7CHO$, to form an alcohol 4 or 4a. Oxidation of the alcohol can be accomplished with oxidants known to those skilled in the art for such purposes such as pyridinium chlorochromate, dimethylsulfoxide and oxalyl chloride, an aqueous solution of chromic acid and sulfuric acid, and the like. Deprotection of the 1-amino group provides the free amine compounds I.

In the processes depicted in Schemes 1 to 8, indoline analogues can serve as intermediates with the indole being subsequently formed by an oxidation reaction. The use of indolines or indoles is presented by the dashed line between carbons 2 and 2a in these Schemes. The oxidation can be effected at any stage which is appropriate in the scheme although normally the oxidation is accomplished as the final step using oxidizing agents as described hereinabove. As indicated hereinabove when indolines are used as reactants in Schemes 1 to 8, Z is preferably trityl whereas triisopropylsilyl is preferably used with indole reactants.

Scheme 2

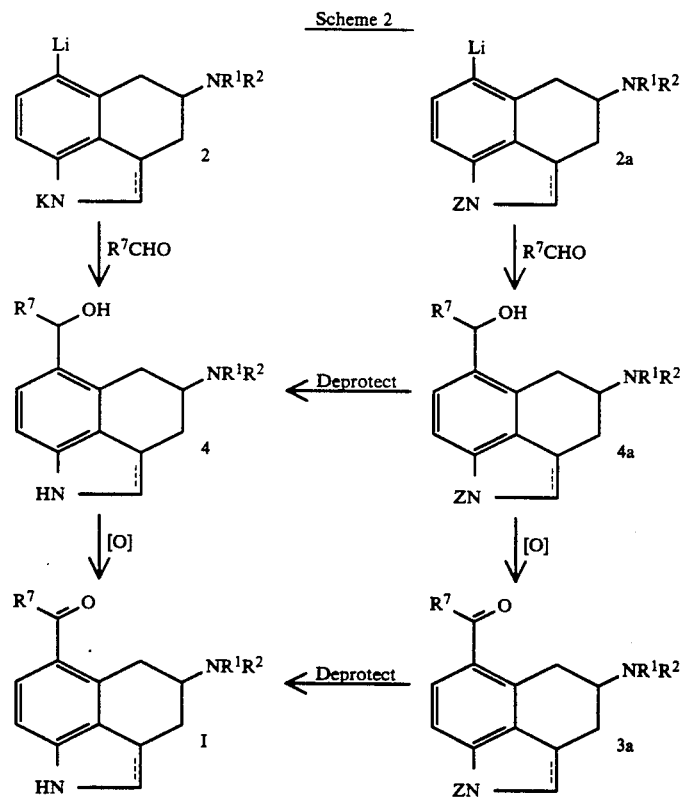

The alcohol intermediates 4 and 4a can alternatively be prepared as depicted in Scheme 3 by addition of an organometallic reagent ($R^7M$) such as an alkyl lithium $R^7Li$ or a Grignard reagent $R^7MgX$ to aldehyde 5 and 5a, respectively.

Scheme 3

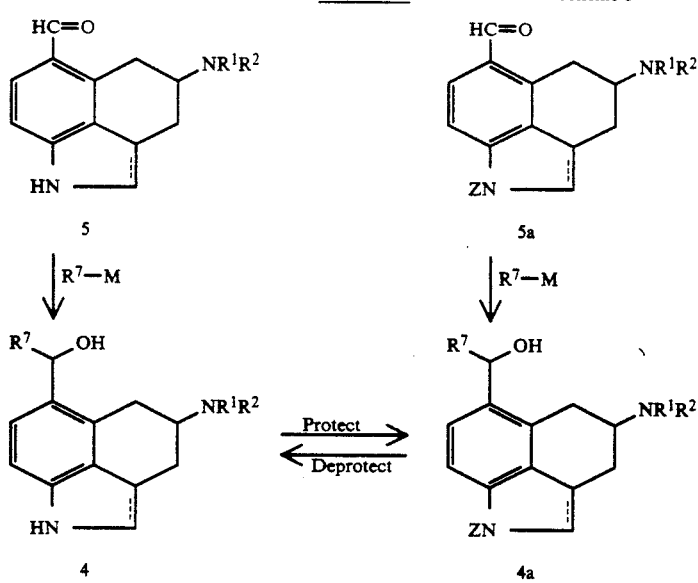

Various routes can be used to prepare aldehydes 5 and 5a. The methods disclosed herein are not intended to be exhaustive and other procedures may be apparent to those skilled in the art. One route involves reacting 6-lithioderivatives 2 and 2a with dimethylformamide followed by aqueous work up. Another method depicted in Scheme 4 involves the preparation of the 6-nitrile derivative 6 followed by reduction and hydrolysis.

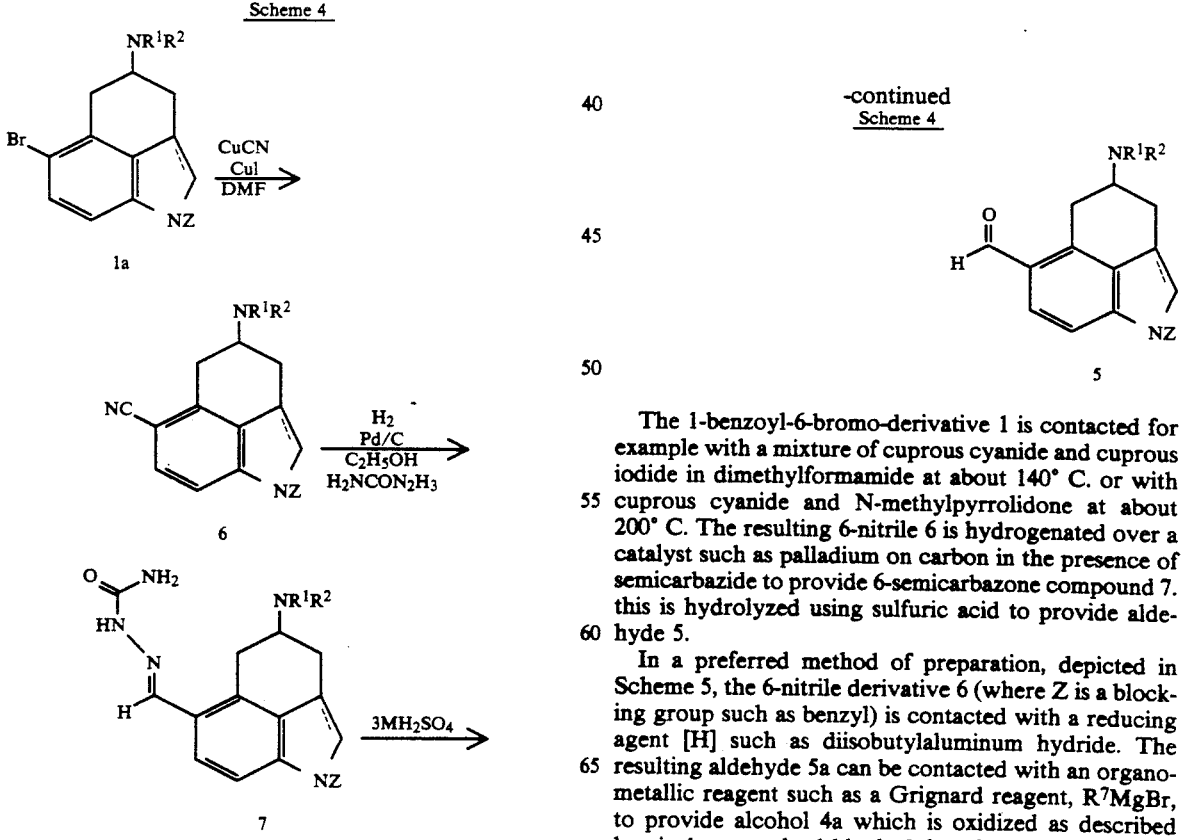

The 1-benzoyl-6-bromo-derivative 1 is contacted for example with a mixture of cuprous cyanide and cuprous iodide in dimethylformamide at about 140° C. or with cuprous cyanide and N-methylpyrrolidone at about 200° C. The resulting 6-nitrile 6 is hydrogenated over a catalyst such as palladium on carbon in the presence of semicarbazide to provide 6-semicarbazone compound 7. this is hydrolyzed using sulfuric acid to provide aldehyde 5.

In a preferred method of preparation, depicted in Scheme 5, the 6-nitrile derivative 6 (where Z is a blocking group such as benzyl) is contacted with a reducing agent [H] such as diisobutylaluminum hydride. The resulting aldehyde 5a can be contacted with an organometallic reagent such as a Grignard reagent, $R^7MgBr$, to provide alcohol 4a which is oxidized as described hereinabove to the 1-blocked-6-acyl derivative 3a.

11

Scheme 5

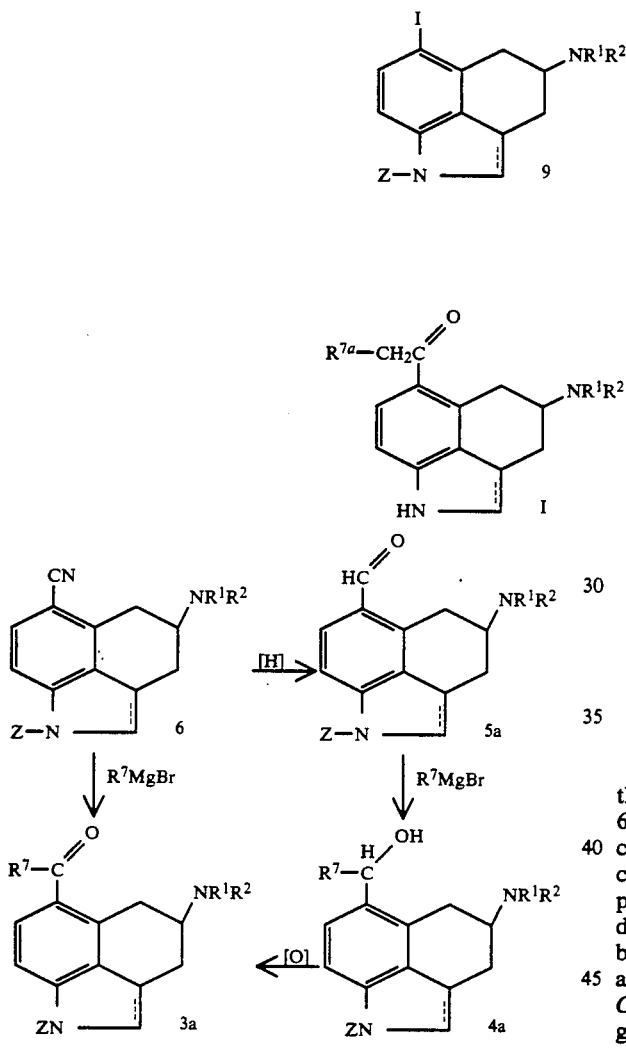

12

HgSO$_4$ in water to provide the ketone 11. The 1-blocking group can be removed by hydrolysis with base as described above to provide compound I.

Scheme 6

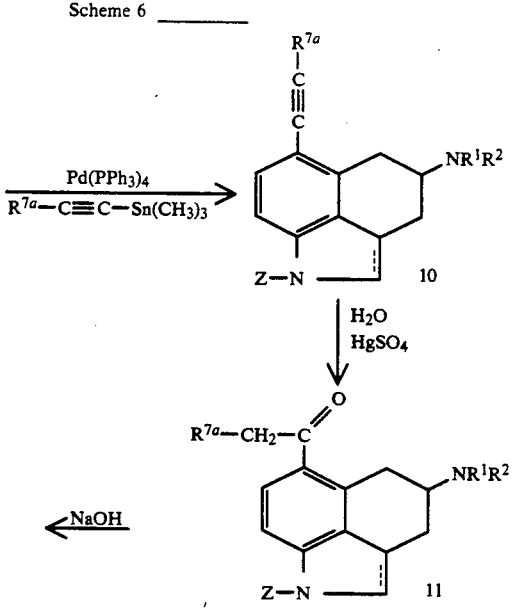

Alternatively, certain compounds of Formula I can be prepared using the 6-iodo derivative 9 as depicted in Schemes 6 and 7 wherein R$^1$, R$^2$ and Z are as defined hereinabove. In Scheme 6 a method is shown in which a 6-alkyne derivative is prepared. This method provides 6-acyl compounds in which there is a methylene group adjacent to the carbonyl group. In this method the 1-nitrogen can be protected with a group (represented by Z) such as a benzoyl group, although the unprotected 1-nitrogen is preferred, i.e. Z is hydrogen. This compound 9 is contacted with a palladium catalyst Pd(PPh$_3$)$_4$ [where Ph is phenyl] and the tin alkyne compound R$^{7a}$—C≡C—Sn—(CH$_3$)$_3$. R$^{7a}$ is a C$_1$-C$_7$ alkyl, substituted C$_1$-C$_7$ alkyl, aryl (C$_1$-C$_3$ alkyl), substituted aryl (C$_1$-C$_3$ alkyl), or C$_3$-C$_7$ cycloalkyl. This reaction is normally conducted in a solvent such as toluene at an elevated temperature, for example at about 100° C. Typically an excess of the tin alkyne is used along about 0.25 equivalents of the palladium compound based on compound 9. The 6-alkyne 10 is then contacted with In another preparation method depicted in Scheme 7, the 6-iodo derivative 9 can be used to prepare certain 6-acyl compounds directly. This is accomplished by contacting the 6-iodo compound with a trialkyltinalkyl complex and carbon monoxide in the presence of a palladium catalyst Pd(PPh$_3$)$_4$ [where Ph is phenyl] as described in the literature for arylhalides. [A. Schoenberg and R. F. Heck, *J. Org. Chem.*, 39, p. 3327 (1974); and A. Schoenberg, I. Bartoletti, and R. F. Heck, *J. Org. Chem.*, 39, p. 3318 (1974)]. Although a blocking group Z such as diethylcarbamoyl can be used for this method, the method can also be accomplished when Z is hydrogen.

Scheme 7

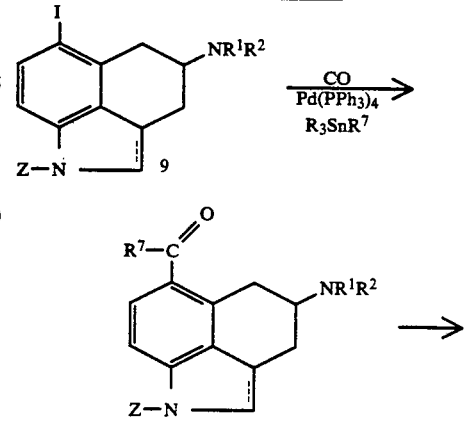

-continued
Scheme 7

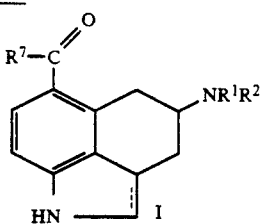

In Scheme 8 a preparative method is depicted in which a vinyl ether is reacted with the 6-iodo derivative 9. $R^1$, $R^2$ and Z are as defined hereinabove. This method provides a 6-(1-alkoxylakenyl) derivative 81 which can then be hydroylzed and deprotected to provide the desired compound of Formula I. Alternatively the derivative 81 can be deprotected, with for example butyl lithium, and then the vinyl group hydrolyzed. In this method the 1-amino group is protected with an amino protecting group, preferably a benzoyl group. This compound 9 is then contacted with a palladium catalyst and the desired vinyl ether. The vinyl ethers useful in this method include those in which $R^C$ is a $C_1$-$C_4$ alkyl and Q is hydrogen or an alkyl tin, alkyl or alkoxy boron, zinc halide, or magnesium halide, for example tributyltin. When Q is zinc halide or magnesium halide, it is preferred that Z be a group such as trityl. $R^a$ and $R^b$ can independently be hydrogen, $C_1$-$C_6$ alkyl, substituted $C_1$-$C_6$ alkyl, aryl, aryl ($C_1$-$C_2$) alkyl, substituted aryl, substituted aryl ($C_1$-$C_2$) alkyl, or $C_3$-$C_7$ cycloalkyl group. The palladium catalyst used can be palladium powder (black) or $Pd(PPh_3)_4$ [where Ph is phenyl]. The $Pd(PPh_3)_4$ is commonly used with toluane at reflux. The Pd-black can be used with triphenylphosphine in toluene at reflux or a mixture of acetonitrite and triethyl amine at about 100° C. Similar reactions are reported in *Bull. Chem. Soc. Jpn.* (1987), 60, 767–768, incorporated herein by reference.

Scheme 8

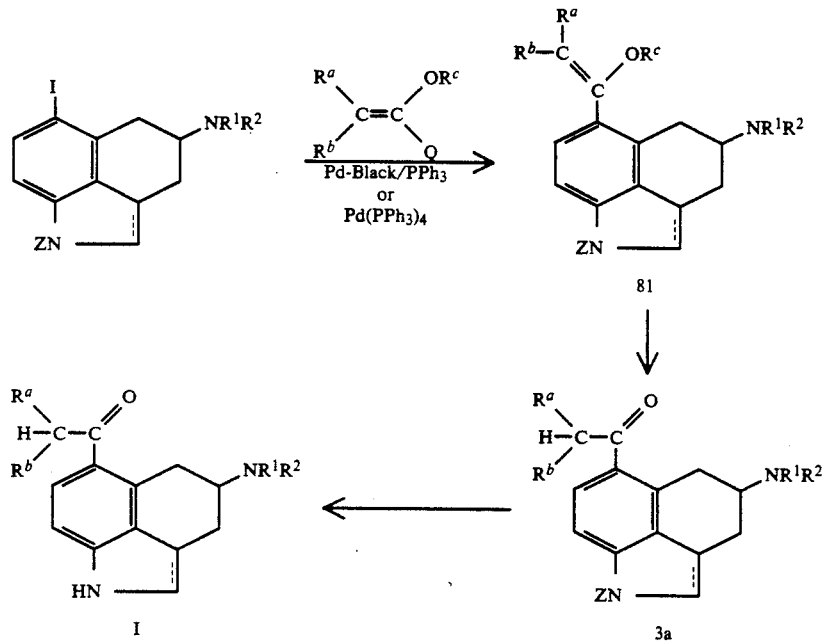

The processes depicted in Schemes 1-8 can result in a mixture of products which require purification by standard methods of purification, for example, crystallization or chromatographic techniques as appropriate.

Scheme 9 illustrates a preparation of the starting material for reaction Scheme 1.

Scheme 9

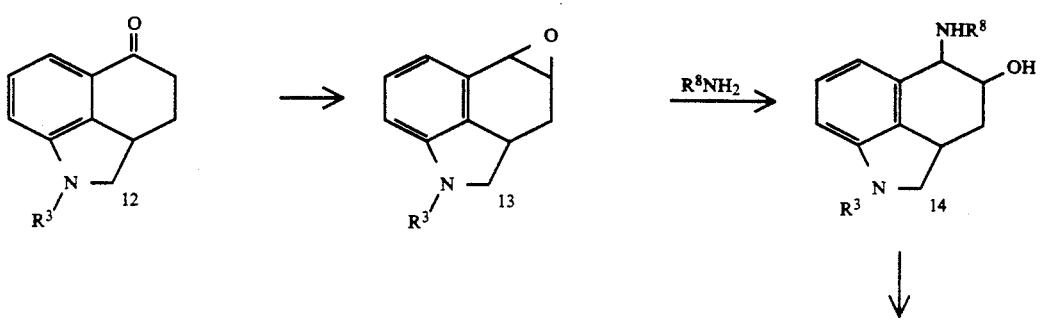

-continued
Scheme 9

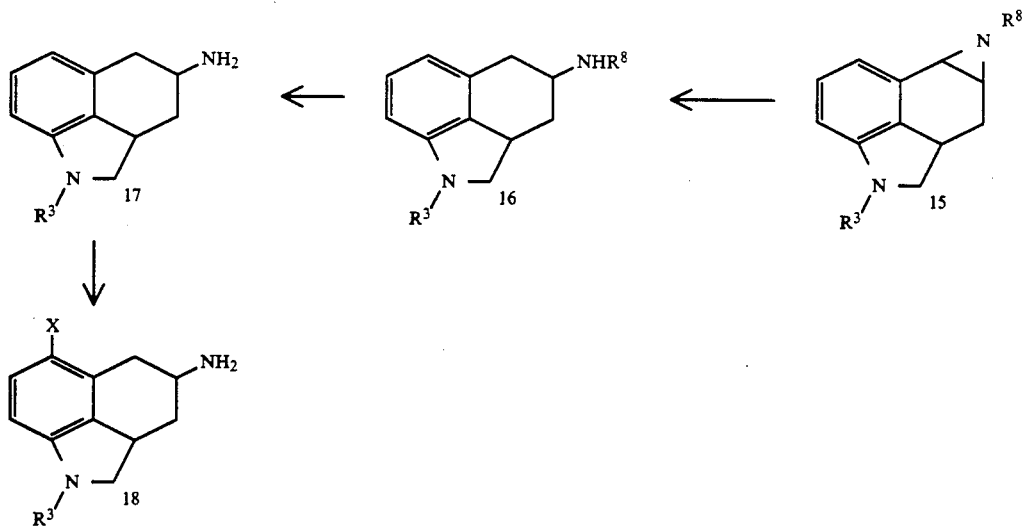

Epoxides of formula 13 are known in the art or can be prepared from compounds such as ketone 12, which is known to the art, using common reagents and techniques. For example, Flaugh, et al., *J. Med. Chem.*, 31, 1746 (1988); Nichols. et al., *Org. Prep. and Proc., Int.*, 9, 277 (1977); and Leanna et al., *Tet. Lett.*, 30, No. 30, 3935 (1989), teach methods of preparation of various embodiments of compounds of formula 13. Those skilled in the art of organic chemistry will recognize that there are four stereoisomers of formula 13:

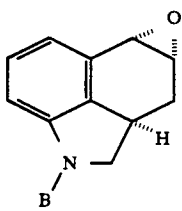 13a

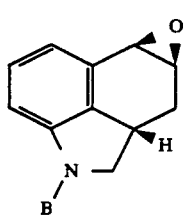 13b

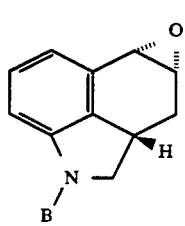 13c

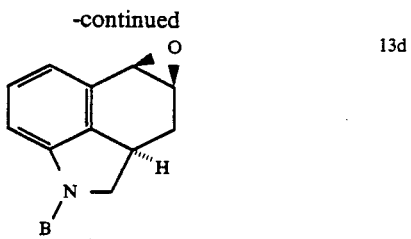 13d

Formulae 13a and 13b are herein referred to collectively as the exo-isomers; similarly, formulae 13c and 13d are the endo-isomers. Leanna et al., supra, teach the preparation of epoxides of formula 13 which are substantially exo or substantially endo, as desired. A preferred starting material is the compound of formula 13 wherein $R^3$ is benzoyl; the most preferred starting material is the mixture of substantially the exo-isomers thereof.

Amino alcohols of formula 14 are formed by reacting an epoxide of formula 13 with an amine of formula $R^8NH_2$, where $R^8$ can be hydrogen, a $C_1-C_4$ alkyl, or a $C_1-C_4$ alkyl substituted with one to three groups selected from halogen, nitro or phenyl. Such amines are readily available. Opening of the epoxide ring proceeds substantially regiospecifically with the amino group at the 5-position and the hydroxyl group at the 4-position. The reaction is also stereospecific in the sense that stereoisomers of formulae 14a-d are predictably formed from, respectively, stereoisomers of formulae 13a-d.

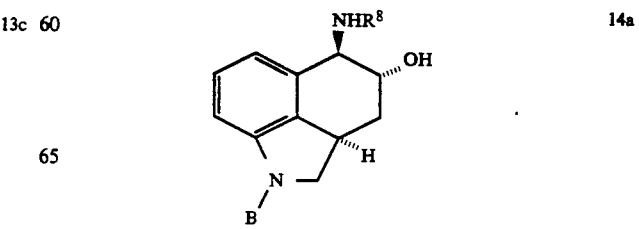 14a

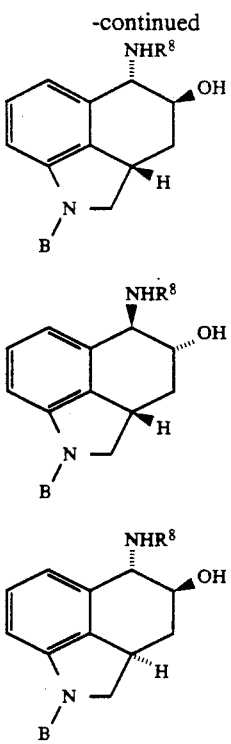

A stereoselective synthesis of the amino alcohol of formula 14, and hence of all the subsequent intermediates and products of Scheme 9, can be effected by using a substantially pure enantiomer of an amine of the formula $R^8NH_2$, wherein $R^8$ contains at least one chiral center. A particularly preferred amine is (+) or (−) 1-phenylethyl amine. The diastereomers of the resulting amino alcohol can then be separated by a number of means known in the art, for example by chromatography or crystallization. Suitable solvents for recrystallization include those such as diethyl ether, butanol, and mixtures of hexane and ethyl acetate. An alternative method of achieving a stereospecific synthesis comprises conversion of all the diastereomers of formula 14 to corresponding diastereomers of formula 15, followed by the separation of said diastereomers of formula 15; that alternative method is discussed below. If a stereoselective synthesis is not desired, then separation of the stereoisomers of the amino alcohol of formula 13 is not required and the amine $R^8NH_2$ need not be optically active.

A particularly efficient stereoselective process for a highly preferred compound of formula 14, 1-benzoyl-4-hydroxy-5-(1-phenylethyl)amino-1,2,2a,3,4,5-hexahydrobenz[cd]indole, comprises the reaction of a mixture of substantially the exo-isomers of the corresponding epoxide of formula 13, or a mixture of substantially the endo-isomers of the corresponding epoxide of formula 13, with a substantially pure enantiomer of 1-phenthylamine in the solvent butanol and the subsequent selective crystallization of one of the two isomers of the amino alcohol. The temperature of the reaction is preferably from about 50° to about 150° C., more preferably in the range of about 80° to about 100° C.

After the reaction is complete, as determined for example by thin layer chromatography of liquid chromatography, the desired amino alcohol is crystallized at about −20° to about 40° C.; the preferred temperature for the crystallization is about 0° to about 15° C. Therefore this process has the valuable attribute that the reaction and the separation of stereoisomers occur efficiently in a single step. By the proper selection of the epoxide isomers, exo or endo, and the enantiomer of 1-phenylethylamine, R or S, one can determine which of the stereoisomers of the compound of formula 14 precipitates from the reaction mixture. For example, a preferred stereoisomer of 1-benzoyl-4-hydroxy-5-(1-phenylethyl)amino-1,2,2a,3,4,5-hexahydrobenz[cd]indole, the (2a,-S,4-R,5-R)-isomer can be selectively prepared by reacting the exo-epoxides with S-1-phenylethylamine.

A number of methods of forming aziridines such as those of formula 15 from amino alcohols such as those of formula 14 are known to the art. Two examples are the use of diethyl azodicarboxylate and triphenylphosphine (O. Mitsunobu, *Synthesis*, Jan., 1981, page 1), and the use of bromine and triphenylphosphine (J. P. Freemer and P. J. Mondron, *Synthesis*, Dec., 1974, page 894).

A particularly efficient alternative to the above methods involving treating a compound of formula 14 with a tertiary amine in an inert solvent followed by the addition of methanesulfonyl chloride. The stereoisomers 15a–d of the aziridine 15 arise respectively from the stereoisomers of formula 14a–d with retention of configuration at any chiral center in the substituents $R^3$ or $R^8$ as well as at position 2a:

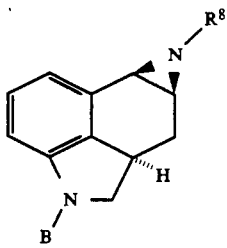

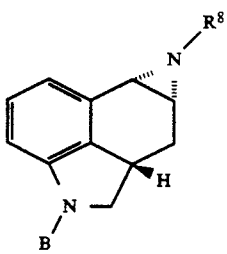

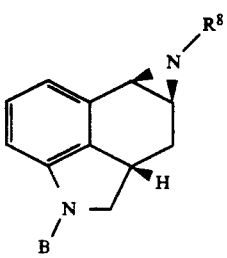

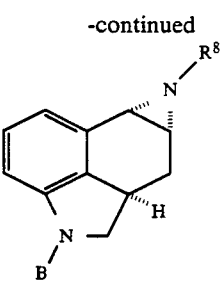

15d

Suitable tertiary amines include those of the formula (R$^9$) N, where the R$^9$ groups are independently C$_1$-C$_4$ alkyl. Suitable solvents are chlorinated hydrocarbons such the compound of formula 16, wherein R$^3$ is benzoyl, and R$^8$ is 1-phenylethyl, include glacial acetic acid or a mixture of methanol and phosphoric acid. The source of hydrogen can be an atmosphere of hydrogen supplied at a pressure of about 1 atmosphere or higher, or the source of hydrogen can be compounds which are suitable to serve as hydrogen donors in a catalytic transfer hydrogenolysis reaction, such as formic acid or hydrazine. The preferred hydrogen source is an atmosphere of hydrogen gas supplied at about 1 to about 10 atmospheres pressure. The temperature of the reaction may be from about −20° to about 80° C.; the preferred temperature for the hydrogenolysis of the aziridine wherein R$^3$ is benzoyl and R$^8$ is 1-phenylethyl is about −20° to about 0° C.

The conversion of compounds of formula 15 to compounds of formula 16 proceeds without disturbing the stereochemical configuration of the chiral centers at the 2a- or 4- positions of the formula 16 or of the chiral centers that may be present in any of the substituents.

If desired, the compound of formula 16 can be isolated by the usual methods such as crystallization. The secondary amine at position 4 of formula 16 can be converted to a primary amine of formula 17 by a number of methods known to the art of organic chemistry, or alternatively the secondary amine itself can be isolated. However, a preferred method is to convert the secondary amine of formula 16 to the primary amine of formula 17 without isolating the secondary amine, but rather by simply continuing without interruption the hydrogenolysis reaction that produced the compound of formula 16. Therefore, the preferred solvent and catalyst are the same as those for the preparation of the secondary amine of formula 16. It may be desirable to conduct the hydrogenolysis of the secondary amine of formula 16 at a different temperature or a different pressure or different temperature and pressure than the hydrogenolysis of the aziridine of formula 15. For the hydrogenolysis of the preferred compound of formula 16 wherein R$^3$ is benzoyl and R$^8$ as methylene chloride, chloroform, carbon tetrachloride, and dichloroethane; aromatic hydrocarbons such as benzene, toluene, and the xylenes; and ethers such as tetrahydrofuran, diethyl ether, and methyl t-butyl ether. The reaction can be conducted at a temperature from about −35° to about 45° C. In the preferred embodiment, the amino alcohol is treated with triethylamine in methylene chloride at about −20° to about 0° C., then the reaction mixture is warmed to about 15° to about 35° C. for the completion of the reaction. If desired, the product, an aziridine of formula 15, can be crystallized from an appropriate solvent such as acetonitrile or isopropanol after an aqueous workup. In the event that R$^8$ contains at least one chiral center in substantially a single stereoconfiguration, the individual stereoisomers of the aziridine of formula 15 can be separated by methods such as chromatography and crystallization, thereby providing a stereospecific synthesis of the aziridine of formula 15 and subsequent products.

The aziridine ring can be opened to form an intermediate secondary amine of formula 16. A number of methods of opening aziridines are commonly known. It is, however, crucial that the method used for opening the aziridine to form a secondary amine of formula 16 be substantially regiospecific, i.e., the aziridine must be opened to form substantially the 4-amino compound rather than the 5-amino compound. One such method is catalytic hydrogenolysis as taught by Y. Sugi and S. Mitsui, Bull, Chem. Soc. Jap., 43, pp. 1489–1496 (1970). Catalysts which are suitable are the usual hydrogenation and hydrogenolysis catalysts, such as the noble metal catalysts; the preferred catalyst is palladium. Suitable solvents include hydrocarbons such as hexanes and heptanes; aromatic hydrocarbons such as benzene, toluene, xylenes, ethylbenzene, and t- butylbenzene; alcohols such as methanol, ethanol, and isopropanol; and mixtures of solvents such as acetic acid mixed with said alcohols. Preferred solvents for preparing is 1-phenylethyl, the preferred temperature and pressure are about 50° to about 60°0 C. and about 1 to about 20 atmospheres. Under these conditions, the hydrogenolysis of compounds of formula 16 to compounds of formula 17 proceeds without disturbing the stereochemical configuration of the chiral center at the 4-position.

The isolation of the compound of formula 17 can be accomplished by the usual methods such as crystallization. If desired, the compound of formula 17 can be further purified, for example by recrystallization.

The compound of formula 17 can be halogenated to provide, for example, the 6-bromo or 6-iodo derivative 18. Iodination of compound 17 can be accomplished by using iodine and orthoperiodic acid in the presence of an acid such as sulfuric acid or trifluoractic acid, in a solvent such as acetic acid. Another method of iodination involves the use of N- iodosuccinimide in the presence of trifluoracetic acid. The 6-bromo derivative can be prepared using bromine in acetic acid or using N-bromosuccinimide.

The formation of the indole by oxidation of the indoline can be effected as depicted in Scheme 9, i.e. as the final step to form structure 19, or it can be accomplished earlier in the process. Appropriate oxidizing agents include MnO$_2$, palladium on carbon, dimethylsulfoxide and oxalyl chloride, and the like.

Of course, as those skilled in the art will recognize, variations of any of the Schemes discussed herein may be desirable or necessary for certain embodiments of the invention. Such variations are contemplated as within the scope of the present invention.

Compounds of Formula I can be prepared from the appropriate compound of formula 19, whether it exists as a mixture of stereoisomers or as a substantially pure enantiomer using common reagents and methods well known in the art. A preferred intermediate to the compounds of the instant invention is the 6-bromo-derivative of 19 although the 6-iodo derivative is preferred if the carbonylation reaction of Scheme 7 is used. Preferably R$^3$ is a blocking group such as benzoyl. Amino blocking groups can be added, if desired, to the 4-amino substituent using such methods as those disclosed by Greene, supra, and Barton, supra. Alkyl groups can be added, if desired, to the 4-amino substituent using such common methods as reaction of the 4-amine with the appropriate halide as discussed by Morrison and Boyd, Chapter 22, *Organic Chemistry*, Third Edition, Allyn and Bacon, Boston, 1973. If desired, the benzoyl group can be removed from the 1-position using known methods and optionally replaced with other amino-protecting groups. The amino-protecting groups and alkyl groups can be added either before or after the bromination, as desired.

The 4-amino-6-bromotetrahydrobenz[cd]indole starting materials used to prepare the compounds of the invention can be readily prepared by other processes such as disclosed in U.S. Pat. No. 4,576,959 and EPO Application Publication No. 0153083 of Flaugh, each of which is incorporated herein by reference in its entirety.

The following examples further illustrate the preparation of the compounds of this invention. The examples are provided for purposes of illustration only and are not to be construed as limiting the scope of the instant invention in any way.

The terms and abbreviations used in the instant examples have their normal meaning unless otherwise designated, for example, "° C." refers to degrees celsius; "N" refers to normal or normality; "mmol" refers to millimole; "g" refers to gram; "ml" or "mL" means milliliter; "M" refers to molar; "min" refers to minutes; "Me" refers to methyl; "Pr" refers to propyl; "Et" refers to ethyl; "THF" refers to tetrahydrofuran; "EtOAc" refers to ethyl acetate; "mp" means melting point; "TLC" refers to thin layer chromatography; "hr" refers to hours; "NMR" refers to nuclear magnetic resonance; "IR" refers to infrared spectroscopy; "U.V." refers to ultraviolet spectroscopy; and "m.s." refers to mass spectrometry.

EXAMPLE 1

Preparation of
(±)-6-(2,2-Dimethylpropanoyl)-4-(di-n-propylamino)-1,3,4,5-tetrahydrobenz[cd]indole A. Preparation of (±)-6-Bromo-1-triisopropylsilyl-4-(di-n-propylamino)-1,3,4,5-tetrahydrobenz[cd]-indole To a suspension of 1.25 g (7.50 mmol) of potassium hydride (24% dispersion in mineral oil) in 50 mL of THF at 0° C. was added a solution of 2.00 g (5.97 mmol) of 6-bromo-4-(di-n-propylamino)-1,3,4,5-tetrahydrobenz[cd]indole in 2 mL of THF. After stirring for 40 min, an addition of 1.90 mL (7.18 mmol) of triisopropylsilyl triflate was made. Stirring was continued for another hour. The mixture was then poured into cold NaHCO$_3$ solution, and the product was extracted into CH$_2$Cl$_2$. This extract was washed with NaCl solution and dried over Na$_2$SO$_4$. Evaporation of the CH$_2$Cl$_2$ left a brown oil which was chromatographed over 50 g of silica gel using toluene followed by 1:3 EtOAc/toluene. The silylated product from the column was isolated as a light brown oil in quantitative yield. The product slowly crystallized upon standing.

B. Preparation of (±)-6-(2,2-Dimethylpropanoyl)-1-triisopropylsilyl-4-(di-n-propylamino)-1,3,4,5-tetrahydrobenz[cd]indole A solution of 0.50 g (1.02 mmol) of the above 1-silylated compound of 20 mL of diethyl ether was stirred at −65° C. as 1.50 mL (2.31 mmol) of 1.54M t-butyllithium (in pentane) was added. After stirring at −70° C. for another 30 minutes, a rapid addition of 0.50 mL (4.00 mmol) of 2,2-dimethylpropionyl chloride was made. The mixture was allowed to warm to −10° C. It was then shaken with 50 mL of cold NaHCO$_3$ solution for several minutes, and the product was extracted into diethyl ether. This extract was washed with NaCl solution and dried over Na$_2$SO$_4$. Evaporation of the ether left an oil which was chromatographed over 7 g of silica gel using 1:19 EtOAc/toluene and then 1:9 EtOCa/toluene. The product from the column was a viscous oil weighing 0.375 g (74% yield).

C. A solution of 0.345 g (0.70 mmol) of the above ketone in 7.0 mL of THF at 0° C. was treated with 1.5 mL of 1M tetrabutylammonium fluoride in THF. After stirring for 30 minutes, the solution was poured into 25 mL of water containing 0.5 g of tartaric acid. This solution was washed with CH$_2$Cl$_2$, and these washings were extracted with fresh dil, tartaric acid solution. The combined aqueous solutions were basifid with 5N NaOH solution, and the product was extracted with CH$_2$Cl$_2$. After drying the extracted over Na$_2$SO$_4$, the solvent was evaporated and the residual oil was chromatographed over 7 g of silica gel using 1:9 EtOAc/toluene. The product from the column crystallized when triturated with hexane. Recrystallization from hexane afforded 0.175 g (88% yield) of (±)-6-(2,2-dimethylpropanoyl)-4-(di-n-propylamino)-1,3,4,5-tetrahydrobenz[cd]indole, mp 92° C.

Analysis for (C$_{22}$H$_{32}$N$_2$O): Theory: C, 77.60; H, 9.47; N, 8.23; Found: C, 77.89; H, 9.37; N, 8.17.

NMR: (300 MHz, CDCl$_3$) δ 0.89 (t, 6H, CCH$_3$ of NPr), 1.31 (s, 9H, CCH$_3$ of Bu$_t$), 1.45 (sextet, 4H, CH$_2$Me), 2.53 (t, 4H, CH$_2$Et), 2.79 (dd, 1H, 3α-H), 2.94 (mult, 2H, 5-CH$_2$), 2.95 (dd, 1H, 3β-H), 3.21 (mult, 1H, 4β-H), 6.87 (s, 1H, 2-H), 7.09 (d, 1H, 8-H), 7.19 (d, 1H, 7- H), 7.91 (s, 1H, 1-H).

EXAMPLE 2

Preparation of
(±)-6-Acetyl-4-(di-n-propylamino)-1,3,4,5-tetrahydrobenz[cd]indole A. Preparation of (±)-6-Cyano-1-triisopropylsilyl-4-(di-n-propylamino)-1,3,4,5-tetrahydrobenz[cd]indole To a suspension of 1.00 g (6.00 mmol) of potassium hyride (24% dispersion in mineral oil) in 25 mL of THF at 0° C. was added 0.90 g (3.20 mmol) of 6-cyano-4-(di-n-propylamino)-1,3,4,5-tetrahydrobenz[c,d]-indole. After stirring for 30 min, an addition of 1.00 mL (3.72 mmol) of triisopropylsilyl triflate was made. The mixture was then stirred at room temp. for 15 hours. It was then poured into cold water, and the product was extracted into CH$_2$Cl$_2$. This extract was washed with NaCl solution and dried over Na$_2$SO$_4$. Evaporation of the CH$_2$Cl$_2$ left a brown oil which was chromatographed over 15 g of silica gel using successively 1:1 hexane/toluene, toluene, and then 1:19 EtOAc/toluene. The silylated product from the column was a light brown oil weighing 0.85 g (62% yield). The product slowly crystallized upon standing.

B. Preparation of (±)-6-Acetyl-1-triisopropylsilyl-4-(di-n-propylamino)-1,3,4,5-tetrahydrobenz[cd]indole A solution of 0.30 g (0.69 mmole) of the above nitrile in 10 mL of benzene was treated with 2.0 mL of 1.0M methylmagnesium bromide in diethyl ether. This mixture was heated at 65° C. for 15 hours. After cooling, the excess Grignard reagent was decomposed with ice chips. The mixture was then stirred for an hour with 10 mL of saturated NH$_4$Cl solution. The benzene layer was separated, and the aqueous layer was extracted with fresh benzene. The combined organic solutions were dried over Na$_2$SO$_4$ then evaporated to a viscous oil. Chromatography of this oil over 5.0 g of silica gel using 1:9 EtOAc/toluene followed by 1:1 EtOAc/toluene afforded 0.29 g (93%) yield) of 6-acetyl compound as a pale yellow oil which slowly crystallized upon standing.

C. A solution of 0.10 g (0.22 mmol) of the above ketone in 2.5 mL of THF at 0° C. was treated with 0.5 mL of 1M tetrabutylammonium fluoride in THF. After stirring for 30 minutes, the solution was poured into 10 mL of water containing 0.2 g of tartaric acid. This solution was washed with CH$_2$Cl$_2$, and these washings were extracted with fresh dil. tartaric acid solution. The combined aqueous solutions were basified with 1N NaOH solution, and the product was extracted with CH$_2$Cl$_2$. After drying the extract over Na$_2$SO$_4$, the solvent was evaporated leaving a crystalline residue. Recrystallization from toluene/hexane afforded 0.045 g (68% yield) of (±)-6-acetyl-4-(di-n-propylamino)-1,3,4,5-tetrahydrobenz[cd]indole, mp 148.5°–150° C.

Analysis for (C$_{19}$H$_{26}$N$_2$O): Theory: C, 76.47; H, 8.78; N, 9.39; Found: C, 76.24; H, 8.85; N, 9.58.

NMR: (300 MHz, CDCl$_3$) δ 0.90 (t, 6H, CCH$_3$ of NPr), 1.48 (sextet, 4H, CH$_2$Me), 1.57 (s, 3H, COCH$_3$), 2.58 (sextet, 4H, CH$_2$Et), 2.78 (dd, 1H, 3α-H), 2.97 (dd, 1H, 3β-H), 3.07 (dd, 1H, 5α-H), 3.20 (mult, 1H, 4β-H), 3.71 (dd, 1H, 5β-H), 6.89 (s, 1H, 2-H), 7.15 (d, 1H, 8-H), 7.66 (d, 1H, 7-H), 8.00 (s, 1H, 1-H).

EXAMPLE 3

Preparation of (±)-6-propanoyl-4-(di-n-propylamino)-1,3,4,5-tetrahydrobenz[cd]indole A solution of 0.52 g (1.19 mmol) of (±)-6-cyano-1-triisoproylsilyl-4-(di-n-propylamino)-1,3,4,5-tetrahydrobenz[cd]indole in 25 mL of benzene was treated with 0.83 mL (1.66 mmol) of 2.0M ethylmagnesium bromide in diethyl ether as in Example 2, part B. Chromatography of the 1-silylated product over silica gel using 1:9 EtOAc/toluene afforded 0.40 g (72% yield) of this material as a light oil. Treatment of this oil in 15 mL of THF with 1.2 mL of 1M tetrabutylammonium fluoride (in THF) as in Example 2, part C gave, after silica gel chromatography (3:7 EtOAc/toluene) and recrystallization from toluene/hexane, 0.157 g (59% yield) of (±)-6-propanoyl-4-(di-n-propylamino)-1,3,4,5-tetrahydrobenz[cd]indole, mp 149°–150° C.

Analysis (C$_{20}$H$_{28}$N$_2$O): Theory: C, 76.88; H, 9.03; N, 8.96; Found: C, 76.60; H, 9.27; N, 8.96.

NMR: (300 MHz, CDCl$_3$) δ 0.91 (t, 6H, CCH$_3$ of NPr), 1.25 (t, 3H, CCH$_3$ of EtCO), 1.48 (sextet, 4H, CH$_2$Me of NPr), 2.58 (sextet, 4H, CH$_2$Et of NPr), 2.78 (dd, 1H, 3α-H), 3.00 (mult, 3H, 3β-H and CH$_2$Me of EtCO), 3.08 (dd, 1H, 5α-H), 3.20 (mult, 1H, 4β-H), 3.70 (dd, 1H, 5β-H), 6.90 (s, 1H, 2-H), 7.16 (d, 1H, 8-H), 7.68 (d, 1H, 7-H), 8.01 (s, 1H, 1-H).

EXAMPLE 4

Preparation of (±)-6-butanoyl-4-(di-n-propylamino)-1,3,4,5-tetrahydrobenz[cd]indole A solution of 0.53 g (1.21 mmol) of (±)-6-cyano-1-triisopropylsilyl-4-(di-n-propylamino)-1,3,4,5-tetrahydrobenz[cd]indole in 25 mL of benzene was treated with 0.61 mL (1.70 mmol) of 2.8M propylamagnesium chloride in diethyl ether as in Example 2, part B. Chromatography of the 1-silylated product over silica gel using 1:9 EtOAc/toluene afforded 0.38 g (65% yield) of this material as a light oil. Treatment of this oil in 15 mL of THF with 1.3 mL of 1M tetrabutylammonium fluoride (in THF) as in Example 2, part C gave, after silica gel chromatography (3:7 EtOAc/toluene) and recrystallization from toluene/hexane, 0.149 g (58% yield) of (±)-6-butanoyl-4-(di-n-propylamino)-1,3,4,5-tetrahydrobenz[cd]indole, mp 151°–153° C.

Analysis (C$_{20}$H$_{28}$N$_2$O): Theory: C, 77.26; H, 9.26; N, 8.58; Found: C, 77.09; H, 9.39; N, 8.44.

NMR: (300 MHz, CDCl$_3$) δ 0.91 (t, 6H, CCH$_3$ of NPr), 1.03 (t, 3H, CCH$_3$ of PrCO), 1.48 (sextet, 4H, CH$_2$Me of NPr), 1.80 (sextet, 2H, CH$_2$Me of PrCO), 2.59 (sextet, 4H, CH$_2$Et of NPr), 2.78 (dd, 1H, 3α-H), 2.97 (mult, 3H, 3β-H and CH$_2$Et of PrCO), 3.08 (dd, 1H, 5α-H), 3.20 (mult, 1H, 4β-H), 3.68 (dd, 1H, 5β-H), 6.90 (s, 1H, 2-H), 7.16 (d, 1H, 8-H), 7.67 (d, 1H, 7-H), 8.03 (s, 1H, 1-H).

EXAMPLE 5

Preparation of (±)-6-(2-methylpropanoyl)-4-(di-n-propylamino)-1,3,4,5-tetrahydrobenz[cd]indole A solution of 0.52 g (1.19 mmol) of (±)-6-cyano-1-triisopropylsilyl-4-(di-n-propylamino)-1,3,4,5-tetrahydrobenz[cd]indole in 25 mL of benzene was treated with 0.85 mL (1.70 mmol) of 2.0M isopropylmagnesium chloride in diethyl ether as in Example 2, part B. Chromatography of the 1-silylated product over silica gel using 1:9 EtOAc/toluene afforded 0.40 g (70% yield) of this material as an oil. Treatment of 0.39 g of this oil in 15 mL of THF with 1.3 mL of 1M tetrabutylammonium fluoride (in THF) as in Example 2, part C gave, after silica gel chromatography (3:7 EtOAc/toluene) and recrystallization from toluene/hexane, 0.106 g (40% yield) of (±)-6-(2-methylpropanoyl)-4-(di-n-propylamino)-1,3,4,5-tetrahydrobenz[cd]indole. mp 127.5°–128° C.

Analysis (C$_{21}$H$_{30}$N$_2$O): Theory: C, 77.26; H, 9.26; N, 8.58; Found: C, 77.03; H, 9.02; N, 8.53.

NMR: (300 MHz, DMSO-d$_6$) δ 0.87 (t, 6H, CCH$_3$ of NPr), 1.07 (d, 3H, CH$_3$ of i-PrCO), 1.12 (d, 3H, CCH$_3$ of i-PrCO), 1.41 (sextet, 4H, CCH$_2$Me of NPr), 2.51 (mult, 4H, CH$_2$Et of NPr), 2.70 (dd, 1H, 3α-H), 2.87 (dd, 1H, 3β-H), 2.95 (dd, 1H, 5α-H), 3.03 (mult, 1H, 4β-H), 3.43 (d, 1H, 5β-H), 3.57 (septet, 1H, CHMe$_2$) 7.04 (s, 1H, 2-H), 7.18 (d, 1H, 8-H), 7.60 (d, 1H, 7-H), 10.92 (s, 1H, 1-H).

EXAMPLE 6

Preparation of (±)-6-benzoyl-4-(di-n-propylamino)-1,3,4,5-tetrahydrobenz[cd]indole Substituting 0.48 mL (4.14 mmol) of benzoyl chloride for the dimethylpropanoyl chloride, the acylation procedure (part B) of Example 1 was repeated. Silica gel chromatography using toluene followed by 1:9 EtOAc/toluene afforded the 1-silylated product as an oil. Treatment of this oil in 15 mL of THF with 2.5 mL of 1M tetrabutylammonium fluoride (in THF) as in Example 2, part C gave, after silica gel chromatography (3:7 EtOAc/toluene) and recrystallization from toluene/hexane, 0.046 g (11% yield) of (±)-6-benzoyl-4-(di-n-propylamino)-1,3,4,5-tetrahydrobenz[cd]indole, mp 149.5°–150.5° C.

Analysis (C$_{24}$H$_{28}$N$_2$O): Theory: C, 79.96; H, 7.83; N, 7.77; Found: C, 79.77; H, 7.79; N, 8.02.

NMR: (300 MHz, CDCl$_3$) δ 0.87 (t, 6H, CCH$_3$), 1.44 (sextet, 4H, CH$_2$Me), 2.50 (t, 4H, CH$_2$Et), 2.82 (dd, 1H, 3α-H), 3.00 (mult, 2H, 3β-H and 5α-H), 3.22 (mult, 1H, 4β-H), 3.28 (dd, 1H, 5β-H), 6.93 (s, 1H, 2-H), 7.14 (d, 1H, 8-H), 7.36 (d, 1H, 7-H), 7.46 (t, 2H, Ph), 7.56 (t, 1H, Ph), 7.82 (d, 2H, Ph), 8.02 (s, 1H, 1-H).

EXAMPLE 7

Preparation of (4R)-(+)-6-acetyl-4-(di-n-propylamino)-1,3,4,5-tetrahydrobenz[cd]indole A. A mixture of 1-benzoyl-4,5-(endo)epoxy-1,2,2a,3,4,5-hexahydrobenz[cd]-indole (21 g, 0.076 mol) and (+)-R-1-phenethylamine (18 g, 0.15 mol) in 400 ml of n-butanol was refluxed under N$_2$ for 16 h. The reaction was concentrated in vacuo to provide 30 g of an oil as an equal mixture of two diastereomeric amino alcohols.

The mixture of amino alcohols was dissolved in 300 ml of CH$_2$Cl$_2$ and Et$_3$N (30 g, 0.225 mol) was added at once under N$_2$. The reaction mixture was cooled to −10° C. then MsCl (12.9 g, 0.011) was slowly added dropwise. The rate of addition was such as to maintain a reaction temperature between −10° and 5° C. Upon complete addition of MsCl, the reaction mixture was stirred for an additional 30 min at −5° C. and then 30 min at ambient temperature. To the reaction mixture was added 200 ml of water and the mixture was stirred. The CH$_2$Cl$_2$ solution was separated and washed successively sat'd NaHCO$_3$ sol and brine sol. The organic sol was dried (MgSO$_4$) and concentrated to dryness to provide a mixture of two diastereomeric aziridines. The mixture was separated by preparative HPLC (silica gel; hexanes/EtOAc gradient). The first diastereomer of the aziridines to be eluted was designated isomer 1; 6.6 g, mp 162°–163° C. from i-PrOH. The second diastereomer to be eluted was designated as isomer 2; 7.4 g, mp 144°–145° C. from isopropyl alcohol.

B. (2aR,4R)-4-amino-1-benzoyl-1,2,2a,3,4,5-hexahydrobenz[cd]indole

A solution of aziridine isomer 1 (9.4 g, 0.025 mol) in 90 ml of glacial acetic acid was hydrogenated at 60 psi and at 60° C. over 5% Pd/C for 16 h. The reaction mixture was filtered and the filtrate was evaporated to a residual oil. The residue was dissolved in 1N HCl and the acidic mixture was extracted once with EtOAC. The acidic solution was made alkaline with addition of concentrated NH$_4$OH. The basic mixture was extracted with CH$_2$Cl$_2$. The CH$_2$Cl$_2$ solution was washed with brine solution and dried (MgSO$_4$). The organic solution was evaporated to dryness to provide 2aR,4R-4-amino-1-benzoyl-1,2,2a,3,4,5-hexhydrobenz[cd] indole; 5.2 g as an oil.

C. (2aR, 4R)-4-amino-1-benzoyl-6-bromo-1,2,2a,3,4,5-hexahydrobenz[cd]indole

A solution of (2aR, 4R)-4-amino-1-benzoyl-1,2,2a,3,4,5-hexahydro-benz[cd]indole (5.2 g, 0.019 mol) and sodium acetate (6.2 g, 0.076) in 40 mL glacial acetic acid (HOAc) and 10 mL of MeOH was cooled to 10° C. to the reaction mixture was added dropwise a solution of bromine (3 g, 0.019 mol) in 10 mL of glacial HOAc. The reaction temperature was maintained at 10° C. during addition of the bromine. The reaction was then stirred at ambient temperature for 1 h. The solvents were evaporated and the residue was dissolved in water. The acidic solution was made alkaline with cold 50% aqueous NaOH. The basic mixture was extracted twice with CH$_2$Cl$_2$. The organic solution was washed with brine solution, dried (MgSO$_4$) and concentrated in vacuo to provide 6.8 g (2aR,4R)-6-bromo compound as an oil.

D. (2aR, 4R)-1-benzoyl-6-bromo-4-(di-n-propylamino)-1,2,2a,3,4,5-hexahydrobenz[cd]indole A reaction mixture of (2aR, 4R)-4-amino-1-benzoyl-6-bromo-1,2,2a,3,4,5-hexahydrobenz[cd]indole (6.8 g, 0.019 mol), K$_2$CO$_3$ (8.28 g, 0.06 mol) and n-propyliodide (10.2 g, 0.06 mol) in 200 mL of CH$_3$CN was stirred at reflux temperature for 16 h. The reaction mixture was filtered and solvent was evaporated. The residue was dissolved in EtOAc and the solution was extracted with dilute HCl. The acidic solution was made alkaline with concentrated NH$_4$OH. The basic mixture was extracted with EtOAc. The organic solution was washed with brine solution and dried (MgSO$_4$). The EtOAc was evaporated to provide a residual oil. Chromatography (silica gel-EtOAc) gave product, 2.4 g.

E. (2aR,4R)-1-Benzoyl-6-cyano-4-(di-n-propylamino)-1,2,2a,3,4,5-hexahydrobenz[cd]indole To a solution of (2aR,4R)-1-Benzoyl-6-bromo-4-(di-n-propylamino)-1,2,2a,3,4,5-hexa-hydrobenz[cd]indole (2.4 g; 5 mmol) in 100 mL of dimethyl formamide (DMF) was added CuCN (1.34 g, 15 mmol) and CuI (2.85 g, 15 mmol). The reaction mixture was stirred at reflux under a N$_2$ atmosphere for 16 hr. The reaction mixture was poured into 500 mL of water. The ppt was collected and washed several times with water. The ppt was suspended in dil NH$_4$OH and slurried with EtOAc. The whole mixture was filtered thru a celite pad. The EtOAc sol was separated and washed with brine sol. The EtOAc sol was dried (MgSO$_4$) and conc to dryness to provide 1.7 g of nitrile as an oil.

F. (2aR,4R)-6-Cyano-4-(di-n-propylamino)-1,2,2a,3,4,5-hexahydrobenz[cd]indole

To a stirred solution of 1.7 g (4.4 mmol) of (2aR,4R)-6-cyano-4-(di-n-propylamino)-1,2,2a,3,4,5-hexahydrobenz[c,d]indole in 25 mL of THF cooled to −78° C. under a N$_2$ atmosphere was added 5.5 mL (8.8 mmol) of 1.6M solution of n-BuLi in hexane. The reaction mixture was stirred at −78° C. for 30 min. and then allowed to warm to −20° C. To the reaction mixture was added 20 mL of 1N NCl. The mixture was extracted once with Et$_2$O. The acidic solution was made alkaline with the addition of cold 5N NaOH. The basic mixture was extracted twice with CH$_2$Cl$_2$. The combined organic solution was washed with sat'd NaCl solution. The CH$_2$Cl$_2$ solution was dried over MgSO$_4$ and evaporated to give 1.3 g of an oil. Chromatography of this oil over silica gel with EtOAc as eluent gave 1 g (80%) of product as an oil.

G. (2aR,4R)-1-Trityl-6-cyano-4-(di-n-propylamino)-1,2,2a,3,4,5-hexahydrobenz[cd]indole To a sol of (2aR,4R)-1-trityl-6-cyano-4-(di-n-propylamino)-1,2,2a,3,4,5-hexahydrobenz[cd]indole (1 g, 3.5 mmol) and Et$_3$N (354 mg, 3.5 mmol) in 50 mL of methylene chloride was added a sol of triphenylmethyl chloride (trityl chloride) (0.98 g, 3.5 mmol) in 10 mL of methylene chloride dropwise at RT. The reaction mixture was stirred for 16 hr at RT. The reaction mixture was extracted with water and cold 1N HCL. The organic sol was washed with sat'd NaHCO$_3$ sol and with sat'd brine sol. The organic sol was dried (MgSO$_4$) and conc to dryness in vacuo to give a residue. The residue was slurried with warm hexanes, cooled and filtered to remove insolubles. The filtrate was conc to an oil. The oil was chromatographed (silica gel, 20% EtOAc in hexanes) to provide 1.5 g of (2aR,4R)-1-trityl-6-cyano-4-(di-n-propylamino)-1,2,2a,3,4,5-hexahydrobenz[cd]indole.

H. (2aR,4R)-6-acetyl-4-(di-n-propylamino)-1,2,2a,3,4,5-hexahydrobenz[c,d]indole

A solution of 1.6 g (3 mmol) (2aR,4R)-1-trityl-6-cyano-4-(di-n-propylamino)-1,2,2a,3,4,5-hexahydrobenz[cd]indole in 100 ml of THF was treated with 20 mL of 2.0M methylmagnesium bromide in diethyl ether. The reaction mixture was refluxed for 16 hr. The reaction mixture was cooled and excess Grignard reagent was decomposed with addition of sat'd NH4Cl solution. The reaction mixture was extracted with EtOAc. The organic solution was evaporated to an oil. The oil was dissolved in 25 mL of 5N HCl and the solution was stirred at room temperature for 30 min. The acidic solution was made alkaline with the addition of excess conc NH4OH solution. The basic mixture was extracted twice with EtOAc. The combined organic solution was washed once with sat'd NaCl solution and dried over MgSO4. The EtOAc solution was evaporated to yield 0.9 g of an oil. Chromatography of this oil over silica gel with EtOAc as eluent gave 600 mg of product. Recryst from hexanes to yield 228 mg (−) ketone.

mp 85°-86°; $[\alpha]_D = -4.94°$ (CH$_3$OH).

I. Formation of the Tetrahydrobenz[cd]indole

A solution of 0.11 g (0.37 mmol) of (2aS,4R)-(+)-6-acetyl-4-(di-n-propylamino)-1,2,2a,3,4,5-hexahydrobenz[c,d]indole and 0.12 g (1 mmol) of indole in 5.0 mL of THF was stirred at 0° C. as 0.075 g (0.21 mmol) of benzeneseleninic anhydride was added. The solution was stirred at 25° C. for 4 hours. It was then poured into dil. tartaric acid solution and washed with CH$_2$Cl$_2$. The aqueous solution was basified with 1N NaOH and extracted with CH$_2$Cl$_2$. An NMR spectrum of the oil obtained upon evaporation of the CH$_2$Cl$_2$ revealed that the oxidation had proceded only to the extent of about 30%. The treatment with benzeneseleninic anhydride as repeated. TLC indicated that a small amount of starting material still remained. The treatment with benzeneseleninic anhydride as carried out a third time, this time with half as much oxidant. The crude product was chromatographed over 3 g of silica gel using 1:9 EtOAc/toluene followed by 1:4 EtOAc/toluene, then recrystallized from toluene/hexane. The purified product weighed 0.033 g (30% yield), mp 135.5°-136° C.

Analysis (C$_{19}$H$_{26}$N$_2$O): Theory: C, 76.47; H, 8.78; N, 9.39; Found: C, 76.31; H, 8.97; N, 9.40.

NMR: Identical to racemate.

$[\alpha]_d = +118°$ (c=5 mg/ml, CH$_3$OH).

EXAMPLE 8

Preparation of (4S)-(−)-6-acetyl-4-(di-n-propylamino)-1,3,4,5-tetrahydrobenz[cd]indole A solution of about 0.15 g (0.50 mmol) of (2aR,4S)-(−)-6-acetyl-4-(di-n-propylamino)-1,2,2a,3,4,5-hexahydrobenz[cd]indole in 10 mL of CH$_2$Cl$_2$ was sonicated (50-55 kHz) in the presence of 1.0 g of MnO$_2$ for 5 hours. The oxidant was removed by filtration through Celite, and the sonication was repeated with 1.0 g of fresh MnO$_2$. The crude product obtained after filtering and removing the solvent was chromatographed over 3 g of silica gel using 1:9 EtOAc/toluene, then recrystallized from toluene/hexane. The purified (4S)-(−)-6-acetyl-4-(di-n-propylamino)-1,3,4,5-tetrahydrobenz[c,d]indole weighed 0.020 g (13% yield), mp 133°-134.5° C.

Analysis (C$_{19}$H$_{26}$N$_2$O): Theory: C, 76.47; H, 8.78; N, 9.39; Found: C, 76.30; H, 9.05; N, 9.39.

NMR: Identical to racemate.

$[\alpha]_D = -121°$ (c=10 mg/ml, CH$_3$OH).

EXAMPLE 9

Preparation of (4R)-(+)-6-(2-methylpropanoyl)-4-(di-n-propylamino)-1,3,4,5-tetrahydrobenz[cd]indole A solution of 0.50 g (1.52 mmol) of (2aS,4R)-(+)-6-(2-methlypropanoyl)-4-(di-n-propylamino)-1,2,2a,3,4,5-hexahydrobenz[cd]indole in 50 mL of hexane was sonicated (50-55 kHz) in the presence of 2.0 g of MnO$_2$ for 6.5 hours. The crude product obtained after filtering and removing the solvent was chromatographed over 3 g of silica gel using 3:7 EtOAc/toluene, then recrystallized from toluene/hexane. The purified (4R)-(+)-6-(2-methylpropanoyl)-4-(di-n-propylamino)-1,3,4,5-tetrahydrobenz[cd]indole weighed 0.120 g (24% yield), mp 148°-150° C.

Analysis (C$_{21}$H$_{30}$N$_2$O): Theory: C, 77.26; H, 9.26; N, 8.58; Found: C, 77.15; H, 9.28; N, 8.69.

NMR: Identical to racemate.

$[\alpha]_D = +87°$ (c=1, CH$_3$OH).

EXAMPLE 10

Preparation of (4R)-(+)-6-benzoyl-4-(di-n-propylamino)-1,3,4,5-tetrahydrobenz[cd]indole A solution of 0.15 g (0.41 mmol) of (2aS,4R)-(+)-6-benzoyl-4-(di-n-propylamino)-1,2,2a,3,4,5-hexahydrobenz[cd indole in 15 mL of hexane was sonicated 50-55 kHz) in the presence of 0.60 g of MnO$_2$ for 4.5 hours. Another 0.15 g of MnO$_2$ was added and the sonication was continued another 2 hours. The crude product obtained after filtering and removing the solvent was chromatographed over 3 g of silica gel using 3:7 EtOAc/toluene, then recrystallized from toluene/hexane. The purified (4R)-(+)-6-benzoyl-4-(di-n-propylamino)-1,3,4,5-tetrahydrobenz[cd]indole weighed 0.050 g (34%) yield), mp 132.5°-134° C.

Analysis (C$_{24}$H$_{28}$N$_2$O): Theory: C, 79.96; H, 7.83; N, 7.77; Found: C, 79.81; H, 7.68; N, 7.60.

NMR: Identical to racemate.

$[\alpha]_D = +122°$ (C=1, CH$_3$OH).

The present compounds of Formula I have been found to have selective affinity for the 5HT receptors in the brain with much less affinity for other receptors. Because of their ability to selectively bind to 5HT receptors, the compounds of Formula I are useful in treating disease states in which alteration of 5HT$_{1A}$ receptor function is beneficial but without the side effects which may be associated with less selective compounds. Certain of the instant compounds have been found to also have substantial affinity for the 5-HT$_{1D}$ receptor and are useful in treating disease states which can be benefitted by alteration of these receptors. The alteration of the particular receptor can involve mimicking (an agonist) or inhibiting (an antagonist) the function of serotonin. The disease states involved include anxiety, depression, excess gastric acid secretion, hypertension, nausea, sexual dysfunction, consumptive disorders such as appetite disorders, alcoholism and smoking, cognition, and senile dementia. The foregoing conditions are treated with a pharmaceutically effective amount of a compound of Formula I.

The term "pharmaceutically effective amount", as used herein, represents an amount of a compound of the invention which is capable of diminishing the adverse symptoms of the particular disease. The particular dose of compound administered according to this invention of course be determined by the particular circumstances surrounding the case, including the compound administered, the route of administration, the particular condition being treated, and similar considerations. The compounds can be administered by a variety of routes including the oral, rectal, transdermal, subcutaneous, intravenous, intramuscular or intranasal routes. A typical single dose for prophylactic treatment, however, will contain from about 0.01 mg/kg to about 50 mg/kg of the active compound of this invention when administered orally. Preferred oral doses are about 0.01 to about 3.0 mg/kg, more preferably about 0.1 to about 1.0 mg/kg. When the compound is given orally it may be necessary to administer the compound more than once each day, for example about every eight hours. For IV administration by bolus, the dose is from about 10 µg/kg to about 300 µg/kg, preferably about 20 µg/kg to about 50 µg/kg.

The following experiments were conducted to demonstrate the ability of the compounds of the present invention to interact with the serotonin 1A and/or 1D receptors. The affinities of the compounds at the central 5-binding assay described by Taylor, et al., (*J. Pharmacol. Exp. Ther.* 236:118–125, 1986). Membranes for the binding assay were prepared from male Sprague-Dawley rats (150–250 g). The animals were killed by decapitation, and the brains were rapidly chilled and dissected to obtain the hippocampi. The hippocampi were either prepared that day or stored frozen (−70° C.) until the day of preparation. Membranes were prepared by homogenizing the tissue in 40 volumes of ice-cold Tris-HCl buffer (50 mM, pH 7.4 at 22° C.) using a Techmar Tissumizer (setting 65 for 15 sec), and the homogenate was centrifuged at 39800 xg for 10 min. The resulting pellet then resuspended in the same buffer, and the centrifugation and resuspension process was repeated three additional times to wash the membranes. Between the second and third washes the resuspended membranes were incubated for 10 min at 37° C. to facilitate the removal of endogenous ligands. The final pellet was resuspended in 67 mM Tris-HCl, pH 7.4, to a concentration of 2 mg of tissue original wet weight/200 µl. This homogenate was stored frozen (−70° C.) until the day of the binding assay. Each tube for the binding assay had a final volume of 800 µl and contained the following: Tris-HCl (50 mM), parggyline (10 µM), CaCl$_2$(3 mM), [$^3$H]8-OH-DPAT (1.0 nM), appropriate dilutions of the compound being evaluated, and membrane resuspension equivalent to 2 mg of original tissue wet weight, for a final pH of 7.4. The assay tubes were incubated for 10 min at 37° C, and the contents were then rapidly filtered through GF/B filters (pretreated with 0.5% polyethylenimine), followed by four one-mL washes with ice cold buffer. The radioactivity trapped by the filters was quantitated by liquid scintillation spectrometry, and specific [$^3$H]8-OH-DPAT binding to the 5-HT$_{1A}$ sites was defined as the difference between [$^3$H]8-OH-DPAT bound in the presence and absence of 10 µM 5-HT.

The affinity of the particular compound at the 5-HT$_{1A}$ receptor is expressed as IC$_{50}$ value, i.e., the concentration required to inhibit 50% of the binding. The IC$_{50}$ values were determined from 12-point competition curves using nonlinear regression (SYSTAT, SYSTAT, INC., Evanston, Ill.). The results from this determination are provided in Table I.

The affinities of the compounds at the central 5-HT$_{1D}$ binding sites were determined using a modification of the binding assay described by Heuring and Peroutka (*J. Neurosci.* 7:894–903, 1987). Bovine brains were obtained from Pel-Freeze Biologicals, and the caudate nuclei were dissected out and frozen at −70° C. until the time that the membranes were prepared for the binding assays. At that time the tissues were homogenized in 40 volumes of ice-cold Tris-HCl buffer (50 mM, pH 7.4 at 22° C.) with a Techmar Tissumizer (setting 65 for 15 sec), and the homogenate was centrifuged at 39,800 g for 10 min. The resulting pellet was then resuspended in the same buffer, and the centrifugation and resuspension process was repeated three additional times to wash the membranes. Between the second and third washes the resuspended membranes were incubated for 10 min at 37° C. to facilitate the removal of endogenous 5-HT. the final pellet was resuspended in Tris buffer to a concentration of 25 mg of original tissue wet weight/ml for use in the binding assay. Each tube for the binding assay had a final volume of 800 µl and contained the following: Tris-HCl (50 mM), parglyine (10 µM), ascorbate (5.7 mM), CaCl$_2$ (3 mM), 8-OH-DPTA (100 nM to mask 5-HT$_{1A}$ receptors), mesulergine (100 nM to mask 5-HT$_{1C}$ receptors), [$^3$H]5-HT (1.7–1.9 nM), appropriate dilutions of the drugs of interest, and membrane suspension equivalent to 5 mg of original tissue wet weight, for a final pH of 7.4. The assay tubes were incubated for 10 min at 37° C., and the contents were then rapidly filtered through GF/B filters (pretreated with 0.5% polyethylenimine), followed by four one-mL washes with ice-cold buffer. The radioactivity trapped by the filters was quantitated by liquid scintillation spectrometry, and specific [$^3$H]5-HT binding to the 5HT$_{1D}$ sites were defined as the difference between [$^3$H]5-HT bound in the presence and absence of 10 µM 5-HT.

The affinities of compounds at the 5-HT1D receptor are expressed as IC$_{50}$ values, i.e., the concentration required to inhibit 50% of the binding. These values were determined from 12-point competition curves using nonlinear regression (SYSTAT, SYSTAT, Inc. Evanston, Ill.). The results from this determination are provided in Table I.

TABLE I

| Example No. | 5HT$_{1A}$[1] | 5HT$_{1D}$[1] |
| --- | --- | --- |
| 1 | 0.50 | 2.01 |
| 2 | 0.2 | 18.37 |
| 7 | 0.22 | 7.46 |
| 8 | 0.12 | 96.37 |
| 9 | 0.16 | 1.27 |
| 10 | 0.22 | 1.81 |

[1]IC$_{50}$ in nanomoles per liter

In another experiment certain compounds of the Examples were evaluated to determine ability to affect the 5-hydroxyindoles serotonin and 5-hydroxyindole acetic acid (5HIAA), and serum corticosterone, in vivo. Male albino rats were injected subcutaneously with an aqueous solution of the compound. The pH of the solution was adjusted as necessary to solubilize the compound. A control of the solution without the test compound was similarly injected into a control animal. The rats were decapitated one hour later. Trunk blood was collected and allowed to clot. After centrifugation, serum was stored frozen prior to analysis. The whole brain was removed and frozen on dry ice for storage prior to analysis. The serum corticosterone concentration was measured spectrofluorometrically using the procedure of Solem and Brinck-Johnson, "An Evaluation of a Method for Determination of Free Corticosteroids in Minute Quantities of Mouse Plasma", Scand. J. Clin. Lab. Invest., Suppl. 80, p. 1-14 (1965), incorporated herein by reference. 5-Hydroxyindoleacetic acid (5HIAA) concentration in whole brain was measured by liquid chromatography with electrochemical detection as reported by Fuller and Perry, "Effects of Buspirone and its Metabolite, 1-(2-pyrimidinyl)piperazine, on Brain Monoamines and Their Metabolites in Rats", J. Pharmacol. Exp. Ther., 248, p. 50-56 (1989), incorporated herein by reference. The results of this procedure are provided in Table II.

TABLE II

| Example No (Dose mg/kg) | Serotonin (nmoles/g) | 5HIAA (nmoles/g) | Serum Corticosterone (microg./100 ml) |
|---|---|---|---|
| Control Example 1 | 2.97 ± 0.27 | 1.55 ± 0.09 | 3.8 ± 0.6 |
| 0.03 | 3.15 ± 0.13 | 1.58 ± 0.05 | 8.2 ± 3.2 |
| 0.3 | 3.45 ± 0.10 | 1.31 ± 0.03(a) | 36.0 ± 4.8(a) |
| 3.0 | 3.38 ± 0.08 | 1.23 ± 0.04(a) | 44.2 ± 1.5(a) |
| Control Example 2 | 2.07 ± 0.08 | 1.62 ± 0.05 | 3.4 ± 0.5 |
| (0.03) | 2.60 ± 0.09(a) | 1.27 ± 0.01(a) | 33.4 ± 3.7(a) |
| (0.3) | 2.54 ± 0.14(a) | 1.10 ± 0.06(a) | 39.1 ± 1.1(a) |
| (3) | 3.25 ± 0.01(a) | 2.04 ± 0.02(a) | 13.8 ± 0.6(a) |
| Control Example 2 | 2.81 ± 0.15 | 2.18 ± 0.05 | 3.4 ± 0.2 |
| (0.0003) | 2.71 ± 0.06 | 2.21 ± 0.05 | 3.8 ± 0.5 |
| (0.003) | 2.64 ± 0.11 | 1.79 ± 0.10(a) | 3.6 ± 0.1 |
| (0.03) | 3.23 ± 0.11 | 1.95 ± 0.04(a) | 36.7 ± 1.2(a) |
| Control Example 7 | 2.08 ± 0.06 | 2.06 ± 0.08 | 4.6 ± 1.0 |
| (0.03) | 2.47 ± 0.07(a) | 1.43 ± 0.02(a) | 41.8 ± 1.7(a) |
| (0.3) | 2.59 ± 0.14(a) | 1.37 ± 0.07(a) | 41.5 ± 5.3(a) |
| (3(b)) | | | |
| Control Example 7 | 2.72 ± 0.10 | 1.81 ± 0.05 | 3.4 ± 0.2 |
| (0.0003) | 2.68 ± 0.11 | 1.93 ± 0.07 | 4.1 ± 0.6 |
| (0.003) | 2.74 ± 0.07 | 1.80 ± 0.05 | 3.6 ± 0.1 |
| (0.03) | 3.00 ± 0.10 | 1.34 ± 0.07(a) | 21.8 ± 2.1(a) |
| Control Example 8 | 2.08 ± 0.06 | 2.06 ± 0.08 | 4.6 ± 1.0 |
| (0.03) | 2.58 ± 0.15(a) | 1.31 ± 0.06(a) | 47.0 ± 2.4(a) |
| (0.3) | 2.78 ± 0.13(a) | 1.36 ± 0.04(a) | 47.3 ± 2.3(a) |
| (3) | 2.63 ± 0.12(a) | 1.35 ± 0.04(a) | 45.4 ± 1.3(a) |
| Control Example 8 | 2.72 ± 0.10 | 1.81 ± 0.05 | 3.4 ± 0.2 |
| (0.0003) | 2.91 ± 0.12 | 1.91 ± 0.08 | 3.4 ± 0.2 |
| (0.003) | 2.65 ± 0.13 | 1.47 ± 0.04(a) | 3.8 ± 0.2 |
| (0.03) | 3.30 ± 0.09(a) | 1.59 ± 0.10 | 40.3 ± 1.8(a) |
| Control(c) Example 8 (c) | 2.55 ± 0.12 | 1.53 ± 0.04 | — |
| (0.1) | 2.77 ± 0.07 | 1.67 ± 0.04(a) | — |
| (0.3) | 2.47 ± 0.07 | 1.60 ± 0.07 | — |
| (1) | 2.86 ± 0.07 | 1.74 ± 0.05(a) | — |
| (3) | 2.68 ± 0.11 | 1.31 ± 0.08(a) | — |
| Control Example 9 | 2.07 ± 0.08 | 1.62 ± 0.05 | 3.4 ± 0.5 |
| (0.03) | 2.56 ± 0.07(a) | 1.38 ± 0.02(a) | 7.7 ± 1.8(a) |
| (0.3) | 2.94 ± 0.13(a) | 1.22 ± 0.04(a) | 40.8 ± 2.0(a) |
| (3) | 2.65 ± 0.07(a) | 1.38 ± 0.08(a) | 30.8 ± 4.5(a) |
| Control Example 9 | 2.81 ± 0.15 | 2.18 ± 0.05 | 3.4 ± 0.2 |
| (0.0003) | 2.76 ± 0.10 | 2.44 ± 0.06(a) | 4.1 ± 0.5 |
| (0.003) | 2.94 ± 0.11 | 2.23 ± 0.09 | 6.0 ± 1.3 |
| (0.03) | 3.08 ± 0.11 | 1.82 ± 0.08(a) | 9.1 ± 1.2(a) |

(a) significant difference from control group (P<0.05).
(b) rats treated with 3 mg/kg were dead within one hour
(c) administered orally 5 hrs before rats were sacrificed.

The compounds of the present invention are preferably formulated prior to administration. Therefore, yet another embodiment of the present invention is a pharmaceutical formulation comprising a compound of the invention and a pharmaceutically acceptable excipient therefor.

The present pharmaceutical formulations are prepared by known procedures using well known and readily available ingredients. In making the compositions of the present invention, the active ingredient will usually be mixed with an excipient, diluted by an excipient or enclosed within such a carrier which can be in the form of a capsule, sachet, paper or other container. When the excipient serves as a diluent, it can be a solid, semi-solid or liquid material which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing for example up to 10% by weight of the active compound, soft and hard gelatin capsules, suppositories, sterile injectable solutions and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include lubricating agents such as talc, magnesium stearate and mineral oil, wetting agents, emulsifying and suspending agents, preserving agents such as methyl- and propylhydroxybenzoates, sweetening agents or flavoring agents. The compositions of the invention may be formulated so as to provide quick, sustained or delayed release of the active ingredient after administration to the patient by employing procedures well known in the art.

The compositions are preferably formulated in a unit dosage form, each dosage containing from about 0.5 to about 50 mg, more usually about 1 to about 10 mg, of the active ingredient. The term "unit dosage form" refers to physically discrete units suitable as unitary dosages for human subjects and other mammals, each unit containing a predetermined quantity of active material calculated to produce the desired therapeutic effect, in association with a suitable pharmaceutical carrier.

The following formulation examples are illustrative only and are not intended to limit the scope of the invention in any way.

FORMULATION 1

Hard gelatin capsules are prepared using the following ingredients:

| | Quantity (mg/capsule) |
|---|---|
| (±)-6-(2,2-Dimethylpropanoyl)- | 25 |

-continued

| | Quantity (mg/capsule) |
|---|---|
| 4-(di-n-propylamino)-1,3,4,5-tetrahydrobenz[cd]indole | |
| Starch, dried | 425 |
| Magnesium stearate | 10 |
| Total | 460 mg |

The above ingredients are mixed and filled into hard gelatin capsules in 460 mg quantities.

FORMULATION 2

A table formula is prepared using the ingredients below:

| | Quantity (mg/tablet) |
|---|---|
| (±)-6-Acetyl-4-(di-n-propylamino)-1,3,4,5-tetrahydrobenz[cd]indole | 25 |
| Cellulose, microcrystalline | 625 |
| Colloidal Silicon dioxide | 10 |
| Stearic acid | 5 |

The components are blended and compressed to form tablets each weighing 665 mg.

FORMULATION 3

A dry powder inhaler formulation is prepared containing the following components:

| | Weight % |
|---|---|
| 4-(diethylamino)-6-propanoyl-1,3,4,5-tetrahydrobenz[cd]-indole | 5 |
| Lactose | 95 |

The active compound is mixed with the lactose and the mixture added to a dry powder inhaling appliance.

FORMULATION 4

Tablets each containing 60 mg of active ingredient are made up as follows:

| | |
|---|---|
| 4-(di-n-propylamino)-6-(2-methylpropanoyl)-1,3,4,5-tetrahydrobenz[cd]indole tartrate salt | 60 mg |
| Starch | 45 mg |
| Microcrystalline cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 150 mg |

The active ingredient, starch and cellulose are passed through a No. 20 mesh U.S. sieve and mixed thoroughly. The solution of polyvinylpyrrolidone is mixed with the resultant powders which are then passed through a No. 4 mesh U.S. sieve. The granules so produced are dried at 50°–60° C. and passed through a No. 16 mesh U.S. sieve. The sodium carboxymethyl starch, magnesium stearate and talc, previously passed through a No. 30 mesh U.S. sieve, are then added to the granule which, after mixing, are compressed on a tablet machine to yield tablets each weighing 150 mg.

FORMULATION 5

Capsules each containing 20 mg of medicament are made as follows:

| | |
|---|---|
| 4-(di-n-propylamino)-6-(3-methylbutanoyl)-1,3,4,5-tetrahydrobenz[cd]indole | 20 mg |
| Starch | 169 mg |
| Magnesium stearate | 1 mg |
| Total | 190 mg |

The active ingredient, cellulose, starch and magnesium stearate are blended, passed through a No. 20 mesh U.S. sieve, and filled into hard gelatin capsules in 190 mg quantities.

FORMULATION 6

Suppositories each containing 225 mg of active ingredient are made as follows:

| | |
|---|---|
| 4-(di-n-propylamino)-6-benzoyl-1,3,4,5-tetrahydrobenz[cd]-indole | 225 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

FORMULATION 7

Suspensions each containing 50 mg of medicament per 5 ml dose are made as follows:

| | |
|---|---|
| 1-methyl-4-(n-propylamino)-6-(3-methylbutanoyl)-1,3,4,5-tetrahydrobenz[cd]indole | 50 mg |
| Xanthan Gum | 4 mg |
| Sodium carboxymethyl cellulose (11%) Microcrystalline Cellulose (89%) | 50 mg |
| Sucrose | 1.75 g |
| Sodium Benzoate | 10 mg |
| Flavor | q.v. |
| Color | q.v. |
| Purified water to | 5 ml |

The medicament, sucrose and xanthan gum are blended, passed through a No. 10 mesh U.S. sieve, and then mixed with a previously made solution of the microcrystalline cellulose and sodium carboxymethylcellulose in water. The sodium benzoate, flavor and color are diluted with some of the water and added with stirring. Sufficient water is then added to produce the required volume.

FORMULATION 8

Capsules each containing 150 mg of medicament are made as follows:

| | |
|---|---|
| 4-(di-n-propylamino)-6-(2-methoxyethanoyl)-1,3,4,5-tetrahydrobenz[cd]-indole | 50 mg |
| Starch | 507 mg |
| Magnesium stearate | 3 mg |
| Total | 560 mg |

The active ingredient, cellulose, starch and magnesium stearate are blended, passed through a No. 20 mesh U.S. sieve, and filled into hard gelatin capsules in 560 mg quantities.

We claim:

1. A compound of the Formula I

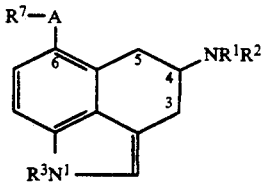

wherein:
- $R^1$ is hydrogen, $C_1$-$C_4$ alkyl, $C_3$-$C_4$ alkenyl, cyclopropylmethyl, phenyl-substituted ($C_1$-$C_4$ alkyl), —C(O)$R^4$, —(CH$_2$)$_n$S($C_1$-$C_4$ alkyl), or —(CH$_2$)$_n$-C(O)NR$^5$R$^6$;
- $R^2$ is hydrogen, $C_1$-$C_4$ alkyl, $C_3$-$C_4$ alkenyl, or cyclopropylmethyl;
- $R^3$ is hydrogen or $C_1$-$C_4$ alkyl;
- n is 1-4;
- $R^4$ is hydrogen, $C_1$-$C_4$ alkyl, $C_1$-$C_4$ haloalkyl, $C_1$-$C_4$ alkoxy or phenyl;
- $R^5$ and $R^6$ are independently hydrogen, a $C_1$-$C_4$ alkyl, or a $C_5$-$C_8$ cycloalkyl;
- A is C=O, CHOH or C≡C;
- $R^7$ is $C_1$-$C_8$ alkyl, trifluoromethyl, $C_1$-$C_8$ alkyl substituted with one or two moieties independently selected from $C_1$-$C_3$ alkoxy, halo, hydroxy and $C_1$-$C_3$ alkylthio, aryl, aryl substituted with one or two moieties independently selected from C-$C_3$ alkoxy, halo, hydroxy, $C_1$-$C_3$ alkylthio, $C_1$-$C_3$ alkyl and trifluoromethyl, aryl ($C_1$-$C_4$ alkyl), aryl ($C_1$-$C_4$ alkyl) substituted with one or two moieties independently selected from $C_1$-$C_3$ alkoxy, halo, hydroxy, $C_1$-$C_3$ alkylthio, $C_1$-$C_3$ alkyl and trifluoromethyl, $C_3$-$C_7$ cycloalkyl-substituted methyl, or $C_3$-$C_7$ cycloalkyl, with the proviso that when A is C≡C then $R^7$ is $C_1$-$C_7$ alkyl, $C_1$-$C_7$ alkyl substituted with one or two moieties independently selected from $C_1$-$C_3$ alkoxy, halo, hydroxy and $C_1$-$C_3$ alkylthio, aryl, aryl substituted with one or two moieties independently selected from $C_1$-$C_3$ alkoxy, halo, hydroxy, $C_1$-$C_3$ alkylthio, $C_1$-$C_3$ alkyl and trifluoromethyl, aryl ($C_1$-$C_3$ alkyl), aryl ($C_1$-$C_3$ alkyl) substituted with one or two moieties independently selected from $C_1$-$C_3$ alkoxy, halo, hydroxy, $C_1$-$C_3$ alkylthio, $C_1$-$C_3$ alkyl and trifluoromethyl, or $C_3$-$C_7$ cycloalkyl; or a pharmaceutically acceptable salt thereof.

2. The compound of claim 1 wherein A is C=O, or a pharmaceutically acceptable salt thereof.

3. The compound of claim 2 wherein
$R^1$ and $R^2$ are independently hydrogen, $C_1$-$C_4$ alkyl, $C_3$-$C_4$ alkenyl, —(CH$_2$)$_n$S($C_1$-$C_4$ alkyl), or cyclopropylmethyl;
$R^3$ is hydrogen or $C_1$-$C_3$ alkyl; n is 2-4; or a pharmaceutically acceptable salt thereof.

4. The compound of claim 3 wherein:
$R^7$ is $C_1$-$C_8$ alkyl, trifluoroemethyl, $C_1$-$C_4$ alkyl substituted with one or two moieties independently selected from $C_1$-$C_3$ alkoxy, halo, hydroxy, and $C_1$-$C_3$ alkylthio, aryl, aryl ($C_1$-$C_4$ alkyl), aryl ($C_1$-$C_4$ alkyl) substituted with one or two moieties independently selected from $C_1$-$C_3$ alkoxy, halo, hydroxy, $C_1$-$C_3$ alkylthio, $C_1$-$C_3$ alkyl and trifluoromethyl or $C_3$-$C_7$ cycloalkyl; or a pharmaceutically acceptable salt thereof.

5. The compound of claim 3 wherein:
$R^7$ is $C_1$-$C_4$ alkyl, trifluoromethyl, $C_1$-$C_3$ alkoxy-substituted ($C_1$-$C_4$ alkyl), phenyl, phenyl ($C_1$-$C_4$ alkyl), halo-substituted phenyl ($C_1$-$C_4$ alkyl), or $C_5$-$C_7$ cycloalkyl; or a pharmaceutically acceptable salt thereof.

6. A substantially pure stereoisomer of the compound of claim 1 or a pharmaceutically acceptable salt thereof.

7. The compound of claim 2 wherein $R^1$ and $R^2$ are independently $C_2$-$C_3$ alkyl; $R^3$ is hydrogen; $R^7$ is $C_1$-$C_3$ alkyl; and pharmaceutically acceptable salts thereof.

8. A compound of claim 1 selected from the group consisting of 4-(di-n-propylamino)-6-acetyl-1,3,4,5-tetrahydrobenz[cd]indole; 4-(di-n-propylamino)-6-(2,2-dimethylpropanoyl)-1,3,4,5-tetrahydrobenz[cd]indole; 4-(diethylamino)-6-propanoyl-1,3,4,5-tetrahydrobenz[cd]indole; 4-(di-n-propylamino)-6-benzoyl-1,3,4,5-tetrahydrobenz [cd]indole; 4-(n-propylamino)-6-(2-methylpropanoyl)-1,3,4,5-tetrahydrobenz[cd]indole; 1-methyl-4-(di-n-propylamino)-6-benzoyl-1,3,4,5-tetrahydrobenz[cd]indole; 1-methyl-4-(n-propylamino)-6-(3-methylbutanoyl)-1,3,4,5-tetrahydrobenz [cd]indole; 4-(di-n-propylamino)-6-(2,2-dimethyl-propanoyl)-1,3,4,5-tetrahydrobenz[cd]indole; 4-(di-n-propylamino)-6-(2-phenylethanoyl)-1,3,4,5-tetrahydrobenz[cd]indole; 4-(N-n-propyl-N-cyclopropylmethyl)amino-6-propanoyl-1,3,4,5-tetrahydrobenz[d]indole; 4-(di-n-propylamino)-6-(2-methoxyethanoyl)-1,3,4,5-tetrahydrobenz[cd]indole; 4-(di-n-propylamino)-6-(2-phenylethanoyl)-1,3,4,5-tetrahydrobenz [cd]indole; or a pharmaceutically acceptable salt thereof.

9. A compound of claim 1 of the formula

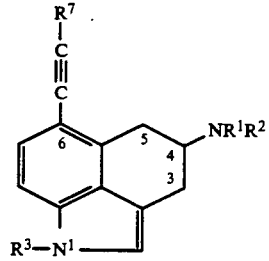

wherein:
- $R^1$ and $R^2$ are independently hydrogen, $C_1$-$C_4$ alkyl, $C_3$-$C_4$ alkenyl, or cyclopropylmethyl;
- $R^3$ is hydrogen or $C_1$-$C_4$ alkyl;
- $R^7$ is $C_1$-$C_7$ alkyl, $C_1$-$C_7$ alkyl substituted with one or two moieties independently selected from $C_1$-$C_3$ alkoxy, halo, hydroxy and $C_1$-$C_3$ alkylthio, aryl, aryl substituted with one or two moieties independently selected from $C_1$-$C_3$ alkoxy, halo, hydroxy, $C_1$-$C_3$ alkylthio, $C_1$-$C_3$ alkyl and trifluoromethyl, aryl ($C_1$-$C_3$ alkyl), aryl ($C_1$-$C_3$ alkyl) substituted with one or two moieties independently selected from $C_1$-$C_3$ alkoxy, halo, hydroxy, $C_1$-$C_3$ alkylthio, $C_1$-$C_3$ alkyl and trifluoromethyl or $C_3$-$C_7$ cycloalkyl.

10. A compound of claim 9 wherein:
$R^1$ and $R^2$ are independently $C_1$-$C_3$ alkyl;
$R^3$ is hydrogen; and
$R^7$ is $C_1$-$C_7$ alkyl, $C_1$-$C_3$ alkoxy-substituted ($C_1$-$C_7$ alkyl), phenyl, phenyl ($C_1$-$C_3$ alkyl), ($C_1$-$C_3$ alkoxy)-substituted phenyl ($C_1$-$C_3$ alkyl), halo-substituted phenyl ($C_1$-$C_3$ alkyl) or $C_3$-$C_7$ cycloalkyl.

11. A substantially pure stereoisomer of the compound of claim 9.

12. A compound of claim 1 of the formula

[Chemical structure: tetrahydronaphthalene with $R^7$-CH(OH) substituent, $NR^1R^2$ substituent, and $R^3$-N= exocyclic methylene]

wherein:
$R^1$ and $R^2$ are independently hydrogen, $C_1$-$C_4$ alkyl, $C_3$-$C_4$ alkenyl, or cyclopropylmethyl;
$R^3$ is hydrogen or $C_1$-$C_4$ alkyl;
$R^7$ is $C_1$-$C_8$ alkyl, trifluoromethyl, $C_1$-$C_8$ alkyl substituted with one or two moieties independently selected from $C_1$-$C_3$ alkoxy, halo, hydroxy and $C_1$-$C_3$ alkylthio, aryl, aryl substituted with one or two moieties independently selected from $C_1$-$C_3$ alkoxy, halo, hydroxy, $C_1$-$C_3$ alkylthio, $C_1$-$C_3$ alkyl and trifluoromethyl, aryl ($C_1$-$C_4$ alkyl), aryl ($C_1$-$C_4$ alkyl) substituted with one or two moieties independently selected from $C_1$-$C_3$ alkoxy, halo, hydroxy, $C_1$-$C_3$ alkylthio, $C_1$-$C_3$ alkyl and trifluoromethyl, or $C_3$-$C_7$ cycloalkyl.

13. A compound of claim 12 wherein:
$R^1$ and $R^2$ are independently $C_1$-$C_4$ alkyl; and
$R^3$ is hydrogen.

14. A compound of the Formula I

[Chemical structure: tetrahydronaphthalene with $R^7$-A substituent, $NR^1R^2$ substituent, and $R^3$-N= exocyclic methylene]

wherein
$R^1$ is hydrogen, $C_1$-$C_4$ alkyl, $C_3$-$C_4$ alkenyl, cyclopropylmethyl, phenyl-substituted ($C_1$-$C_4$ alkyl), —C(O)$R^4$, —(CH$_2$)$_n$S($C_1$-$C_4$ alkyl), or —(CH$_2$)$_n$-C(O)NR$^5$R$^6$;
$R^2$ is hydrogen, $C_1$-$C_4$ alkyl, $C_3$-$C_4$ alkenyl, or cyclopropylmethyl;
$R^3$ is an amino-blocking group;
n is 1-4;
$R^4$ is hydrogen, $C_1$-$C_4$ alkyl, $C_1$-$C_4$ haloalkyl, $C_1$-$C_4$ alkoxy or phenyl;

$R^5$ and $R^6$ are independently hydrogen, $C_1$-$C_4$ alkyl, or $C_5$-$C_8$ cycloalkyl;
A is C=O, CHOH or C≡C;
$R^7$ is $C_1$-$C_8$ alkyl, trifluoromethyl, $C_1$-$C_8$ alkyl substituted with one or two moieties independently selected from $C_1$-$C_3$ alkoxy, halo, hydroxy and $C_1$-$C_3$ alkylthio, aryl, aryl substituted with one or two moieties independently selected from $C_1$-$C_3$ alkoxy, halo, hydroxy, $C_1$-$C_3$ alkylthio, $C_1$-$C_3$ alkyl and trifluoromethyl, aryl ($C_1$-$C_4$ alkyl), aryl ($C_1$-$C_4$ alkyl) substituted with one or two moieties independently selected from $C_1$-$C_3$ alkoxy, halo, hydroxy, $C_1$-$C_3$ alkylthio, $C_1$-$C_3$ alkyl and trifluoromethyl, $C_3$-$C_7$ cycloalkyl-substituted methyl, or $C_3$-$C_7$ cycloalkyl with the proviso that when A is C≡C then $R^7$ is $C_1$-$C_7$ alkyl, $C_1$-$C_7$ alkyl substituted with one or two moieties independently selected from $C_1$-$C_3$ alkoxy, halo, hydroxy and $C_1$-$C_3$ alkylthio, aryl, aryl substituted with one or two moieties independently selected from $C_1$-$C_3$ alkoxy, halo, hydroxy, $C_1$-$C_3$ alkylthio, $C_1$-$C_3$ alkyl and trifluoromethyl, aryl ($C_1$-$C_3$ alkyl), aryl ($C_1$-$C_3$ alkyl) substituted with one or two moieties independently selected from $C_1$-$C_3$ alkoxy, halo, hydroxy, $C_1$-$C_3$ alkylthio, $C_1$-$C_3$ alkyl and trifluoromethyl, or $C_3$-$C_7$ cycloalkyl; or a pharmaceutically acceptable salt thereof.

15. A compound of claim 14 wherein A is C=O or a pharmaceutically acceptable salt thereof.

16. A compound of claim 14 wherein A is CHOH or a pharmaceutically acceptable salt thereof.

17. A compound of claim 14 wherein A is C≡C or a pharmaceutically acceptable salt thereof.

18. A method for treating anxiety in humans comprising administering to a human suffering from anxiety an effective antianxiety dose of a compound of claim 1.

19. A method for treating depression in humans comprising administering to a human suffering from depression an effective dose of a compound of claim 1.

20. A pharmaceutical formulation comprising a compound of claim 1 or a pharmaceutically acceptable salt thereof in combination with a pharmaceutically acceptable excipient.

21. The formulation of claim 20 wherein said compound has the formula

[Chemical structure: tetrahydronaphthalene with $R^7$-C(=O)- substituent, $NR^1R^2$ substituent, and $R^3$-N= exocyclic methylene]

or pharmaceutically acceptable salt thereof.

* * * * *

UNITED STATES PATENT AND TRADEMARK OFFICE
CERTIFICATE OF CORRECTION

PATENT NO. : 5,229,409
DATED : July 20, 1993
INVENTOR(S) : Michael E. Flaugh, et. al.

It is certified that error appears in the above-indentified patent and that said Letters Patent is hereby corrected as shown below:

Column 35, line 34, delete "C-C3", and insert therefor --C1-C3--.
Column 35, line 63, delete "trifluoroemethyl" and insert therefor --trifluoromethyl--.
Column 36, line 14, delete "and pharmaceutically acceptable salts" and insert therefor --or a pharmaceutically acceptable salt.--
Column 36, line 30, delete "tetrahydrobenz[d]" and insert therefor--tetrahydrobenz[cd]...--.

Signed and Sealed this

Eleventh Day of October, 1994

Attest:

BRUCE LEHMAN

*Attesting Officer*  *Commissioner of Patents and Trademarks*